United States Patent [19]

Banner et al.

[11] Patent Number: 5,597,899
[45] Date of Patent: Jan. 28, 1997

[54] TUMOR NECROSIS FACTOR MUTEINS

[75] Inventors: David Banner, Basle; Werner Lesslauer, Riehen; Hansruedi Lötscher, Möhlin, all of Switzerland; Dietrich Stüber, Grenzach–Wyhlen, Germany

[73] Assignee: Hoffmann-La Roche Inc., Nutley, N.J.

[21] Appl. No.: 217,529

[22] Filed: Mar. 24, 1994

[30] Foreign Application Priority Data

Mar. 29, 1993 [EP] European Pat. Off. ............ 93810224

[51] Int. Cl.$^6$ .......................... C07K 14/525; C12P 21/06
[52] U.S. Cl. ...................... 530/351; 435/69.5; 435/69.1; 530/402
[58] Field of Search .......................... 530/351; 435/69.1, 435/69.5

[56] References Cited

U.S. PATENT DOCUMENTS

| | | | |
|---|---|---|---|
| 4,179,337 | 12/1979 | Davis et al. | 435/181 |
| 4,650,674 | 3/1987 | Aggarwal et al. | |
| 4,948,875 | 8/1990 | Tanaka et al. | |
| 4,990,455 | 2/1991 | Yamagishi et al. | |

FOREIGN PATENT DOCUMENTS

| | | |
|---|---|---|
| 40162 | 7/1989 | Australia . |
| 155549 | 9/1985 | European Pat. Off. . |
| 168214 | 1/1986 | European Pat. Off. . |
| 251037 | 1/1988 | European Pat. Off. . |
| 486908 | 5/1992 | European Pat. Off. . |
| 526905 | 2/1993 | European Pat. Off. . |
| 563714 | 10/1993 | European Pat. Off. . |
| 3843534 | 7/1990 | Germany . |
| 88/06625 | 9/1988 | WIPO . |

OTHER PUBLICATIONS

Yamagishi et al., "Mutational analysis of structure—activity relationships in human tumor necrosis factor–alpha", Protein Engineering 3:713–719 (1990).

Van Ostade et al., "Localization of the active site of human tumour necrosis factor (hTNF) by mutational analysis", EMBO J. 10:827–836 (1991).

Zhang et al., "Site–directed mutational analysis of human tumor necrosis factor–α receptor binding site and structure–functional relationship", J. Biol. Chem. 267:24069–24075 (1992).

Derwent Abstract Japanese Patent Appl. Publ. No. 03061495.

Fiers, "TNF: mechanisms of action in vitro and in vivo", in Influence of Molecular Biology on Drug Discovery ed. Udaka et al. (Munich, W. Zuckerschwerdt Verlag 1989) pp. 17–24.

Fiers, "Precursor structures and structure/function analysis of the TNF and lymphotoxin", in Tumor Necrosis Factors: Structure, Function and Mechanism of Action, ed. Aggarwal and Vilcek (Marcel Dekker, New York 1992), pp. 79–92.

Fiers, "In vitro and in vivo action of tumor necrosis factor", in Tumor Necrosis Factor: Structure, Mechanism of Action, Role in Disease and Therapy, ed. Bonavida and Granger, (S. Karger, Basel, 1990), pp. 77–81.

Fiers et al., "Lymphokines and monokines in anti–cancer therapy", in Cold Spring Harbor Symposium on Quantitative Biology, vol. LI (Cold Spring Harbor, 1986) pp. 587–595.

Mackay et al., "Tumor necrosis factor α (TNF–α)–induced cell adhesion to human endothelial cells is under dominant control of one TNF receptor type, TNF–R55", J. Exp. Med. 177:1277–1286 (1993).

Loetscher et al., "Human tumor necrosis factor α (TNFα) mutants with exclusive specificity for the 55–kDa TNF receptors", J. Biol. Chem. 268:26350–26357 (1993).

Loetscher et al., "Activation of TNF receptors: structural and functional aspects", 8th Symposium Molecular Biology Hematopoiesis, Basel, Jul. 9–13, (Manuscript No. B 161 605).

Angehrn et al., "Two distinct tumor necrosis factor receptors in health and disease", in Tumor Necrosis Factor: Molecular and Cellular Biology and Clinical Relevance, ed. Fiers & Buurman (Karger, Basle (1993)) pp. 33–39.

Warren et al., "The acute metabolic effects of tumor necrosis factor administration in humans", Arch Sur, 122:1396–1400 (1987).

Taguchi et al., "Clinical studies with TNF", Biotherapy 3:177–186 (1991).

Brouckaert et al., "In vivo anti–tumour activity of recombinant human and murine TNF, alone and in combination with murine IFN–γ, on a syngeneic murine melanoma", Int. J. Cancer 38:763–769 (1986).

Van Ostade et al., "Human TNF mutants with selective activity on the p55 receptor", Nature 361:266–269 (1993).

Tartaglia and Goeddel, "Two TNF receptors", Immunology Today 13:151–153 (1992).

Barrett et al., "Cloning, expression and cross–linking analysis of the murine p55 tumor necrosis factor receptor", Eur. J. Immunol. 21:1649–1656 (1991).

Lewis et al., "Cloning and expression of cDNAs for two distinct murine tumor necrosis factor receptors demonstrate one receptor is species specific", Proc. Natl. Acad. Sci. USA 88:2830–2834 (1991).

Tsujimoto et al., "Comparative studies of the biological activities of human tumor necrosis factor and its derivatives", J. Biochem. 101:919–925 (1987).

(List continued on next page.)

*Primary Examiner*—Robert A. Wax
*Assistant Examiner*—Karen Cochrane Carlson
*Attorney, Agent, or Firm*—George W. Johnston; William H. Epstein; Catherine R. Smith

[57] ABSTRACT

Human TNF muteins having higher binding affinity for human p75-TNF receptor than for human p55-TNF receptor include muteins having at least one different amino acid relative to wild-type human TNF at a position corresponding to position 33, 65, 67, 75, 87, 143, 145 or 147 of the wild-type amino acid sequence.

10 Claims, 12 Drawing Sheets

OTHER PUBLICATIONS

Goh et al., "Aspartic acid 50 and tyrosine 108 are essential for receptor binding and cytotoxic activity of tumour necrosis factor beta (lymphotoxin)", Protein Eng. 4:785–791 (1991).

Carlino et al., "Use of a sensitive receptor binding assay to discriminate between full–length and truncated human recombinant tumor necrosis factor proteins", J. Biol. Chem. 262:958–961 (1987).

Tavernier et al., "Analysis of the structure–function relationship of tumour necrosis factor. Human/mouse chimeric TNF proteins: general properties and epitope analysis", J. Mol. Biol. 211:493–502 (1990).

Eck et al., "The structure of tumor necrosis factor–$\alpha$ at 2.6 Å resolution", J. Biol. Chem. 264:17595–17605 (1989).

Yamagishi et al., Protein Eng. 3(4), 1990 p. 372 (abstract only).

Masegi et al., "Fundamental studies on novel recombinant tumor necrosis factor mutants", Protein Eng. 375–376 (1989).

Tsukio, "Novel physiologically active polypeptide", Patent Abstract of Japan, vol. 13, No. 119 (1989).

Lesslauer et al., "Cell–associated and soluble TNF receptors: perspective of new therapeutic strategies", in Maurice Rapin Colloquia Mediators of Sepsis: From Pathophysiology to Therapetic Approaches (Manuscript No. 161 230) (Paris, Flammarion 1993).

Cunningham et al., "Receptor and antibody epitopes in human growth hormone identified by homolog–scanning mutagenesis", Science 243:1330–1336 (1989).

Goh and Porter, "Structural and functional domains in human tumour necrosis factors", Protein Eng. 4:385–389 (1991).

Pennica et al, "Human tumour necrosis factor: precursor structure, expression and homology to lymphotoxin", Nature 312:724–729 (1984).

```
        XhoI
  1     CTCGAGAAAT   CATAAAAAAT   TTATTTGCTT   TGTGAGCGGA   TAACAATTAT
                                               EcoRI
 51     AATAGATTCA   ATTGTGAGCG   GATAACAATT   TCACACAGAA   TTCATTAAAG

101     AGGAGAAATT   AAGCATGGTC   AGATCATCTT   CTCGAACCCC   GAGTGACAAG
                            Val   ArgSerSerS   erArgThrPr   oSerAspLys
                              1                                     11

151     CCTGTAGCCC   ATGTTGTCGC   GAACCCTCAA   GCTGAGGGGC   AGCTCCAGTG
        ProValAlaH   isValValAl   aAsnProGln   AlaGluGlyG   lnLeuGlnTr
                                          21

BglI
201     GCTGAACCGC   CGGGCCAATG   CCCTCCTGGC   CAATGGCGTG   GAGCTGAGAG
        pLeuAsnArg   ArgAlaAsnA   laLeuLeuAl   aAsnGlyVal   GluLeuArgA
                31                                     41

251     ATAACCAGCT   GGTGGTGCCA   TCAGAGGGCC   TGTACCTCAT   CTACTCCCAG
        spAsnGlnLe   uValValPro   SerGluGlyL   euTyrLeuIl   eTyrSerGln
                             51                                     61

301     GTCCTCTTCA   AGGGCCAAGG   CTGCCCCTCC   ACCCATGTGC   TCCTCACCCA
        ValLeuPheL   ysGlyGlnGl   yCysProSer   ThrHisValL   euLeuThrHi
                                          71

351     CACCATCAGC   CGCATCGCCG   TCTCCTACCA   GACCAAGGTC   AACCTCCTCT
        sThrIleSer   ArgIleAlaV   alSerTyrGl   nThrLysVal   AsnLeuLeuS
                81                                     91

401     CTGCCATCAA   GAGCCCCTGC   CAGAGGGAGA   CCCCAGAGGG   GGCTGAGGCC
        erAlaIleLy   sSerProCys   GlnArgGluT   hrProGluGl   yAlaGluAla
                              101                                  111

451     AAGCCCTGGT   ATGAGCCCAT   CTATCTGGGA   GGGGTCTTCC   AGCTGGAGAA
        LysProTrpT   yrGluProIl   eTyrLeuGly   GlyValPheG   lnLeuGluLy
                                         121

501     GGGTGACCGA   CTCAGCGCTG   AGATCAATCG   GCCCGACTAT   CTCGACTTTG
        sGlyAspArg   LeuSerAlaG   luIleAsnAr   gProAspTyr   LeuAspPheA
               131                                    141

551     CCGAGTCTGG   GCAGGTCTAC   TTTGGGATCA   TTGCCCTGTG   AGGAGGACGA
        laGluSerGl   yGlnValTyr   PheGlyIleI   leAlaLeu
                                         151           157
```

*FIG. 1B-1*

| | | | | |
|---|---|---|---|---|
| 601 | ACATCCAACC | TTCCCAAACG | CCTCCCTCG | CCCAATCCCT | TTATTACCCC |
| 651 | CTCCTTCAGA | CACCCTCAAC | CTCTTCTGGC | TCAAAAGAG | AATTGGGGGC |
| 701 | TTAGGGTCGG | *HindIII* AACCCAAGCT | TGGACTCCTG | TTGATAGATC | CAGTAATGAC |
| 751 | CTCAGAACTC | CATCTGGATT | TGTTCAGAAC | GCTCGGTTGC | CGCCGGGCGT |
| 801 | TTTTTATTGG | TGAGAATCCA | AGCTAGCTTG | GCGAGATTTT | CAGGAGCTAA |
| 851 | GGAAGCTAAA | ATGGAGAAAA | AAATCACTGG | ATATACCACC | GTTGATATAT |
| 901 | CCCAATGGCA | TCGTAAAGAA | CATTTTGAGG | CATTTCAGTC | AGTTGCTCAA |
| 951 | TGTACCTATA | ACCAGACCGT | TCAGCTGGAT | ATTACGGCCT | TTTTAAAGAC |
| 1001 | CGTAAAGAAA | AATAAGCACA | AGTTTTATCC | GGCCTTTATT | CACATTCTTG |
| 1051 | CCCGCCTGAT | GAATGCTCAT | CCGGAATTTC | GTATGGCAAT | GAAAGACGGT |
| 1101 | GAGCTGGTGA | TATGGGATAG | TGTTCACCCT | TGTTACACCG | TTTTCCATGA |
| 1151 | GCAAACTGAA | ACGTTTTCAT | CGCTCTGGAG | TGAATACCAC | GACGATTTCC |
| 1201 | GGCAGTTTCT | ACACATATAT | TCGCAAGATG | TGGCGTGTTA | CGGTGAAAAC |
| 1251 | CTGGCCTATT | TCCCTAAAGG | GTTTATTGAG | AATATGTTTT | TCGTCTCAGC |
| 1301 | CAATCCCTGG | GTGAGTTTCA | CCAGTTTTGA | TTTAAACGTG | GCCAATATGG |
| 1351 | ACAACTTCTT | CGCCCCCGTT | TTCACCATGG | GCAAATATTA | TACGCAAGGC |
| 1401 | GACAAGGTGC | TGATGCCGCT | GGCGATTCAG | GTTCATCATG | CCGTCTGTGA |
| 1451 | TGGCTTCCAT | GTCGGCAGAA | TGCTTAATGA | ATTACAACAG | TACTGCGATG |
| 1501 | AGTGGCAGGG | CGGGGCGTAA | TTTTTTTAAG | GCAGTTATTG | GTGCCCTTAA |
| 1551 | ACGCCTGGGG | TAATGACTCT | CTAGCTTGAG | GCATCAAATA | AAACGAAAGG |
| 1601 | CTCAGTCGAA | AGACTGGGCC | TTTCGTTTTA | TCTGTTGTTT | GTCGGTGAAC |
| 1651 | GCTCTCCTGA | GTAGGACAAA | *XbaI* TCCGCCGCTC | TAGAGCTGCC | TCGCGCGTTT |
| 1701 | CGGTGATGAC | GGTGAAAACC | TCTGACACAT | GCAGCTCCCG | GAGACGGTCA |

*FIG. 1B-2*

| 1751 | CAGCTTGTCT | GTAAGCGGAT | GCCGGGAGCA | GACAAGCCCG | TCAGGGCGCG |
| 1801 | TCAGCGGGTG | TTGGCGGGTG | TCGGGCGCA | GCCATGACCC | AGTCACGTAG |
| 1851 | CGATAGCGGA | GTGTATACTG | GCTTAACTAT | GCGGCATCAG | AGCAGATTGT |
| 1901 | ACTGAGAGTG | CACCATATGC | GGTGTGAAAT | ACCGCACAGA | TGCGTAAGGA |
| 1951 | GAAAATACCG | CATCAGGCGC | TCTTCCGCTT | CCTCGCTCAC | TGACTCGCTG |
| 2001 | CGCTCGGTCT | GTCGGCTGCG | GCGAGCGGTA | TCAGCTCACT | CAAAGGCGGT |
| 2051 | AATACGGTTA | TCCACAGAAT | CAGGGGATAA | CGCAGGAAAG | AACATGTGAG |
| 2101 | CAAAAGGCCA | GCAAAAGGCC | AGGAACCGTA | AAAAGGCCGC | GTTGCTGGCG |
| 2151 | TTTTTCCATA | GGCTCCGCCC | CCTGACGAG | CATCACAAAA | ATCGACGCTC |
| 2201 | AAGTCAGAGG | TGGCGAAACC | CGACAGGACT | ATAAAGATAC | CAGGCGTTTC |
| 2251 | CCCCTGGAAG | CTCCCTCGTG | CGCTCTCCTG | TTCCGACCCT | GCCGCTTACC |
| 2301 | GGATACCTGT | CCGCCTTTCT | CCCTTCGGGA | AGCGTGGCGC | TTTCTCAATG |
| 2351 | CTCACGCTGT | AGGTATCTCA | GTTCGGTGTA | GGTCGTTCGC | TCCAAGCTGG |
| 2401 | GCTGTGTGCA | CGAACCCCCC | GTTCAGCCCG | ACCGCTGCGC | CTTATCCGGT |
| 2451 | AACTATCGTC | TTGAGTCCAA | CCCGGTAAGA | CACGACTTAT | CGCCACTGGC |
| 2501 | AGCAGCCACT | GGTAACAGGA | TTAGCAGAGC | GAGGTATGTA | GGCGGTGCTA |
| 2551 | CAGAGTTCTT | GAAGTGGTGG | CCTAACTACG | GCTACACTAG | AAGGACAGTA |
| 2601 | TTTGGTATCT | GCGCTCTGCT | GAAGCCAGTT | ACCTTCGGAA | AAAGAGTTGG |
| 2651 | TAGCTCTTGA | TCCGGCAAAC | AAACCACCGC | TGGTAGCGGT | GGTTTTTTTG |
| 2701 | TTTGCAAGCA | GCAGATTACG | CGCAGAAAAA | AAGGATCTCA | AGAAGATCCT |
| 2751 | TTGATCTTTT | CTACGGGGTC | TGACGCTCAG | TGGAACGAAA | ACTCACGTTA |
| 2801 | AGGGATTTTG | GTCATGAGAT | TATCAAAAAG | GATCTTCACC | TAGATCCTTT |
| 2851 | TAAATTAAAA | ATGAAGTTTT | AAATCAATCT | AAAGTATATA | TGAGTAAACT |
| 2901 | TGGTCTGACA | GTTACCAATG | CTTAATCAGT | GAGGCACCTA | TCTCAGCGAT |

FIG. 1B-3

| 2951 | CTGTCTATTT | CGTTCATCCA | TAGCTGCCTG | ACTCCCCGTC | GTGTAGATAA |
| --- | --- | --- | --- | --- | --- |
| 3001 | CTACGATACG | GGAGGGCTTA | CCATCTGGCC | CCAGTGCTGC | AATGATACCG |
| 3051 | CGAGACCCAC | GCTCACCGGC | TCCAGATTTA | TCAGCAATAA | ACCAGCCAGC |
| 3101 | BglI<br>CGGAAGGGCC | GAGCGCAGAA | GTGGTCCTGC | AACTTTATCC | GCCTCCATCC |
| 3151 | AGTCTATTAA | TTGTTGCCGG | GAAGCTAGAG | TAAGTAGTTC | GCCAGTTAAT |
| 3201 | AGTTTGCGCA | ACGTTGTTGC | CATTGCTACA | GGCATCGTGG | TGTCACGCTC |
| 3251 | GTCGTTTGGT | ATGGCTTCAT | TCAGCTCCGG | TTCCCAACGA | TCAAGGCGAG |
| 3301 | TTACATGATC | CCCCATGTTG | TGCAAAAAG | CGGTTAGCTC | CTTCGGTCCT |
| 3351 | CCGATCGTTG | TCAGAAGTAA | GTTGGCCGCA | GTGTTATCAC | TCATGGTTAT |
| 3401 | GGCAGCACTG | CATAATTCTC | TTACTGTCAT | GCCATCCGTA | AGATGCTTTT |
| 3451 | CTGTGACTGG | TGAGTACTCA | ACCAAGTCAT | TCTGAGAATA | GTGTATGCGG |
| 3501 | CGACCGAGTT | GCTCTTGCCC | GGCGTCAATA | CGGGATAATA | CCGCGCCACA |
| 3551 | TAGCAGAACT | TTAAAAGTGC | TCATCATTGG | AAAACGTTCT | TCGGGGCGAA |
| 3601 | AACTCTCAAG | GATCTTACCG | CTGTTGAGAT | CCAGTTCGAT | GTAACCCACT |
| 3651 | CGTGCACCCA | ACTGATCTTC | AGCATCTTTT | ACTTTCACCA | GCGTTTCTGG |
| 3701 | GTGAGCAAAA | ACAGGAAGGC | AAAATGCCGC | AAAAAAGGGA | ATAAGGGCGA |
| 3751 | CACGGAAATG | TTGAATACTC | ATACTCTTCC | TTTTTCAATA | TTATTGAAGC |
| 3801 | ATTTATCAGG | GTTATTGTCT | CATGAGCGGA | TACATATTTG | AATGTATTTA |
| 3851 | GAAAAATAAA | CAAATAGGGG | TTCCGCGCAC | ATTTCCCCGA | AAAGTGCCAC |
| 3901 | CTGACGTCTA | AGAAACCATT | ATTATCATGA | CATTAACCTA | TAAAAATAGG |
| 3951 | CGTATCACGA | GGCCCTTTCG | TCTTCAC | | |

*FIG. 1B-4*

|      | HindIII    |            |            |            |            |
|------|------------|------------|------------|------------|------------|
| 1    | AAGCTTCACG | CTGCCGCAAG | CACTCAGGGC | GCAAGGGCTG | CTAAAGGAAG |
| 51   | CGGAACACGT | AGAAAGCCAG | TCCGCAGAAA | CGGTGCTGAC | CCCGGATGAA |
| 101  | TGTCAGCTAC | TGGGCTATCT | GGACAAGGGA | AAACGCAAGC | GCAAAGAGAA |
| 151  | AGCAGGTAGC | TTGCAGTGGG | CTTACATGGC | GATAGCTAGA | CTGGGCGGTT |
| 201  | TTATGGACAG | CAAGCGAACC | GGAATTGCCA | GCTGGGGCGC | CCTCTGGTAA |
| 251  | GGTTGGGAAG | CCCTGCAAAG | TAAACTGGAT | GGCTTTCTTG | CCGCCAAGGA |
| 301  | TCTGATGGCG | CAGGGGATCA | AGATCTGATC | AAGAGACAGG | ATGACGGTCG |
| 351  | TTTCGCATGC | TTGAACAAGA | TGGATTGCAC | GCAGGTTCTC | CGGCCGCTTG |
| 401  | GGTGGAGAGG | CTATTCGGCT | ATGACTGGGC | ACAACAGACA | ATCGGCTGCT |
| 451  | CTGATGCCGC | CGTGTTCCGG | CTGTCAGCGC | AGGGGCGCCC | GGTTCTTTTT |
| 501  | GTCAAGACCG | ACCTGTCCGG | TGCCCTGAAT | GAACTGCAGG | ACGAGGCAGC |
| 551  | GCGGCTATCG | TGGCTGGCCA | CGACGGGCGT | TCCTTGCGCA | GCTGTGCTCG |
| 601  | ACGTTGTCAC | TGAAGCGGGA | AGGGACTGGC | TGCTATTGGG | CGAAGTGCCG |
| 651  | GGGCAGGATC | TCCTGTCATC | TCACCTTGCT | CCTGCCGAGA | AAGTATCCAT |
| 701  | CATGGCTGAT | GCAATGCGGC | GGCTGCATAC | GCTTGATCCG | GCTACCTGCC |
| 751  | CATTCGACCA | CCAAGCGAAA | CATCGCATCG | AGCGAGCACG | TACTCGGATG |
| 801  | GAAGCCGGTC | TTGTCGATCA | GGATGATCTG | GACGAAGAGC | ATCAGGGGCT |
| 851  | CGCGCCAGCC | GAACTGTTCG | CCAGGCTCAA | GGCGCGCATG | CCCGACGGCG |
| 901  | AGGATCTCGT | CGTGACCCAT | GGCGATGCCT | GCTTGCCGAA | TATCATGGTG |
| 951  | GAAAATGGCC | GCTTTTCTGG | ATTCATCGAC | TGTGGCCGGC | TGGGTGTGGC |
| 1001 | GGACCGCTAT | CAGGACATAG | CGTTGGCTAC | CCGTGATATT | GCTGAAGAGC |
| 1051 | TTGGCGGCGA | ATGGGCTGAC | CGCTTCCTCG | TGCTTTACGG | TATCGCCGCT |
| 1101 | CCCGATTCGC | AGCGCATCGC | CTTCTATCGC | CTTCTTGACG | AGTTCTTCTG |

*FIG. 2B-1*

| | | | | | |
|---|---|---|---|---|---|
| 1151 | AGCGGGACTC | TGGGGTTCGA | AATGACCGAC | CAAGCGACGC | CCAACCTGCC |
| 1201 | ATCACGAGAT | TTCGATTCCA | CCGCCGCCTT | CTATGAAAGG | TTGGGCTTCG |
| 1251 | GAATCGTTTT | CCGGGACGCC | GGCTGGATGA | TCCTCCAGCG | CGGGGATCTC |
| 1301 | ATGCTGGAGT | TCTTCGCCCA | CCCCGGGCTC | GATCCCCTCG | CGAGTTGGTT |
| 1351 | CAGCTGCTGC | CTGAGGCTGG | ACGACCTCGC | GGAGTTCTAC | CGGCAGTGCA |
| 1401 | AATCCGTCGG | CATCCAGGAA | ACCAGCAGCG | GCTATCCGCG | CATCCATGCC |
| 1451 | CCCGAACTGC | AGGAGTGGGG | AGGCACGATG | GCCGCTTTGG | SalI<br>TCGACAATTC |
| 1501 | GCGCTAACTT | ACATTAATTG | CGTTGCGCTC | ACTGCCCGCT | TTCCAGTCGG |
| 1551 | GAAACCTGTC | GTGCCAGCTG | CATTAATGAA | TCGGCCAACG | CGCGGGGAGA |
| 1601 | GGCGGTTTGC | GTATTGGGCG | CCAGGGTGGT | TTTTCTTTTC | ACCAGTGAGA |
| 1651 | CGGGCAACAG | CTGATTGCCC | TTCACCGCCT | GGCCCTGAGA | GAGTTGCAGC |
| 1701 | AAGCGGTCCA | CGCTGGTTTG | CCCCAGCAGG | CGAAAATCCT | GTTTGATGGT |
| 1751 | GGTTAACGGC | GGGATATAAC | ATGAGCTGTC | TTCGGTATCG | TCGTATCCCA |
| 1801 | CTACCGAGAT | ATCCGCACCA | ACGCGCAGCC | CGGACTCGGT | AATGGCGCGC |
| 1851 | ATTGCGCCCA | GCGCCATCTG | ATCGTTGGCA | ACCAGCATCG | CAGTGGGAAC |
| 1901 | GATGCCCTCA | TTCAGCATTT | GCATGGTTTG | TTGAAAACCG | GACATGGCAC |
| 1951 | TCCAGTCGCC | TTCCCGTTCC | GCTATCGGCT | GAATTTGATT | GCGAGTGAGA |
| 2001 | TATTTATGCC | AGCCAGCCAG | ACGCAGACGC | GCCGAGACAG | AACTTAATGG |
| 2051 | GCCCGCTAAC | AGCGCGATTT | GCTGGTGACC | CAATGCGACC | AGATGCTCCA |
| 2101 | CGCCCAGTCG | CGTACCGTCT | TCATGGGAGA | AAATAATACT | GTTGATGGGT |
| 2151 | GTCTGGTCAG | AGACATCAAG | AAATAACGCC | GGAACATTAG | TGCAGGCAGC |
| 2201 | TTCCACAGCA | ATGGCATCCT | GGTCATCCAG | CGGATAGTTA | ATGATCAGCC |

FIG. 2B-2

| 2251 | CACTGACGCG | TTGCGCGAGA | AGATTGTGCA | CCGCCGCTTT | ACAGGCTTCG |
| 2301 | ACGCCGCTTC | GTTCTACCAT | CGACACCACC | ACGCTGGCAC | CCAGTTGATC |
| 2351 | GGCGCGAGAT | TTAATCGCCG | CGACAATTTG | CGACGGCGCG | TGCAGGGCCA |
| 2401 | GACTGGAGGT | GGCAACGCCA | ATCAGCAACG | ACTGTTTGCC | CGCCAGTTGT |
| 2451 | TGTGCCACGC | GGTTGGGAAT | GTAATTCAGC | TCCGCCATCG | CCGCTTCCAC |
| 2501 | TTTTTCCCGC | GTTTTCGCAG | AAACGTGGCT | GGCCTGGTTC | ACCACGCGGG |
| 2551 | AAACGGTCTG | ATAAGAGACA | CCGGCATACT | CTGCGACATC | GTATAACGTT |
| 2601 | ACTGGTTTCA | CATTCACCAC | CCTGAATTGA | CTCTCTTCCG | GGCGCTATCA |
| 2651 | TGCCATACCG | CGAAAGGTTT | TGCGCCATTC | GATGGTGTCA | ACGTAAATGC |
| | | | SalI | | |
| 2701 | ATGCCGCTTC | GCCTTCGCGC | GCGAATTGTC | GACCCTGTCC | CTCCTGTTCA |
| 2751 | GCTACTGACG | GGGTGGTGCG | TAACGGCAAA | AGCACCGCCG | GACATCAGCG |
| 2801 | CTAGCGGAGT | GTATACTGGC | TTACTATGTT | GGCACTGATG | AGGGTGTCAG |
| 2851 | TGAAGTGCTT | CATGTGGCAG | GAGAAAAAAG | GCTGCACCGG | TGCGTCAGCA |
| 2901 | GAATATGTGA | TACAGGATAT | ATTCCGCTTC | CTCGCTCACT | GACTCGCTAC |
| 2951 | GCTCGGTCGT | TCGACTGCGG | CGAGCGGAAA | TGGCTTACGA | ACGGGGCGGA |
| 3001 | GATTTCCTGG | AAGATGCCAG | GAAGATACTT | AACAGGGAAG | TGAGAGGGCC |
| 3051 | GCGGCAAAGC | CGTTTTTCCA | TAGGCTCCGC | CCCCCTGACA | AGCATCACGA |
| 3101 | AATCTGACGC | TCAAATCAGT | GGTGGCGAAA | CCCGACAGGA | CTATAAAGAT |
| 3151 | ACCAGGCGTT | TCCCCTGGCG | GCTCCCTCGT | GCGCTCTCCT | GTTCCTGCCT |
| 3201 | TTCGGTTTAC | CGGTGTCATT | CCGCTGTTAT | GGCCGCGTTT | GTCTCATTCC |
| 3251 | ACGCCTGACA | CTCAGTTCCG | GGTAGGCAGT | TCGCTCCAAG | CTGGACTGTA |
| 3301 | TGCACGAACC | CCCCGTTCAG | TCCGACCGCT | GCGCCTTATC | CGGTAACTAT |

FIG. 2B-3

| | | | | | |
|---|---|---|---|---|---|
| 3351 | CGTCTTGAGT | CCAACCCGGA | AAGACATGCA | AAAGCACCAC | TGGCAGCAGC |
| 3401 | CACTGGTAAT | TGATTTAGAG | GAGTTAGTCT | TGAAGTCATG | CGCCGGTTAA |
| 3451 | GGCTAAACTG | AAAGGACAAG | TTTTGGTGAC | TGCGCTCCTC | CAAGCCAGTT |
| 3501 | ACCTCGGTTC | AAAGAGTTGG | TAGCTCAGAG | AACCTTCGAA | AAACCGCCCT |
| 3551 | GCAAGGCGGT | TTTTTCGTTT | TCAGAGCAAG | AGATTACGCG | CAGACCAAAA |
| 3601 | CGATCTCAAG | AAGATCATCT | TATTAATCAG | ATAAAATATT | TCTAGATTTC |
| 3651 | AGTGCAATTT | ATCTCTTCAA | ATGTAGCACC | TGAAGTCAGC | CCCATACGAT |
| 3701 | ATAAGTTGTT | AATTCTCATG | TTTGACAGCT | TATCATCGAT | |

*FIG. 2B-4*

TUMOR NECROSIS FACTOR MUTEINS

The present invention relates to Tumor Necrosis Factor Muteins.

BACKGROUND OF THE INVENTION

Tumor Necrosis Factor, or more specifically Tumor Necrosis Factor-α (for ease of reference, unless otherwise indicated, "Tumor Necrosis Factor" or "TNF" when used herein refers to TNF-α), is a cytokine, primarily produced by stimulated macrophages. It exhibits not only a striking cytotoxicity against various tumour cells [Carswell et al., Procd. Nat. Acad. Sci., USA 72, 3666–3670, (1975)] but also plays a multiple role as a mediator of inflammation and the immune response [for an overview see Beutler and Cerami, Ann. Rev. Immunol. 7, 625–655 (1989); Bonavista and Granger (eds.) "Tumor Necrosis Factor: Structure, Mechanism of Action, Role in Disease and Therapy, Karger, Basel (1990)". The primary structure of human Tumor Necrosis Factor-α (hTNF-α) has been deduced from the nucleotide sequence of a cDNA which has been cloned and expressed in E. coli [Pennica et al., Nature 312, 724–729 (1984); Marmenout et al., Europ. J. Biochem. 152, 515–522 (1985); Wang et al., Science 228, 149–154 (1985); Shirai et al., Nature 313, 803–806 (1985)]. A striking homology in amino acid sequence (30%) was found between hTNF-α and human Lymphotoxin, often referred to as human Tumor Necrosis Factor-beta (hTNF-β), a cytokine mainly produced by activated lymphocytes [Gray et al., Nature 312, 721–724 (1984); Fiers et al., Cold Spring Harbour Symp. 51, 587–595 (1986)].

hTNF-α with modified amino acid sequences, so called TNF-α-muteins, have also been described in various publications—for example Yamagishi et al., Protein Engineering 3, 713–719, (1990); Fiers in "Tumor Necrosis Factors: Structure, Function and Mechanism of Action"; Fiers et al. in Bonavista and Granger, pp. 77–81 (see above); Goh et al., (1991), "Structural and functional domains in human tumor necrosis factors." Prot. Engineering 4: 385–389; Kircheis et al., (1992), "Biological activity of mutants of human tumor necrosis factor-α, "Immunology 76: 433–438; Van Ostade et al., (1991), "Localization of the active site of human tumor necrosis factor (hTNF) by mutational analyses," EMBO J. 10: 827–836; Van Ostade et al., (1993), "Human TNF mutants with selective activity on the p55 receptor," Nature 361: 266–269; Zhang et al., (1992), "Site-directed mutational analysis of human tumor necrosis factor-α receptor binding site and structure-functional relationship," J. Biol. Chem. 267: 24069–24075; and in Ito et al., (1991), "Novel muteins of human tumor necrosis factor α, "Biochim. Biophys. Acta 1096: 245–252. In addition TNF-α-muteins have been the object of several patent applications, e.g. International Patent Applications Publ. Nos. WO 86/02381, WO 86/04606, WO 88/06625 and European Patent Applications Publ. Nos. 155,549; 158,286; 168,214; 251,037 and 340,333, and Deutsche Offenlegungsschrift Nr. 3843534.

Muteins of Lymphotoxin have also been disclosed in the art, e.g. in European Patent Applications Publ. Nos. 250,000; 314,094 and 336,383, as well as in the following two publications: Goh et al., (1991), "Aspartic acid 50 and tyrosine 108 are essential for receptor binding and cytotoxic activity of tumor necrosis factor beta (lymphotoxin)," Prot. Engineering 4: 785–791 and Wakabayashi et al., (1990), "Deletion of lysine 89 enhances the cytotoxicity and the receptor binding affinity of human lymphotoxin," J. Biol. Chem. 265: 7604–7609.

The biological effects of TNF are mediated via specific receptors, namely a receptor with an apparent molecular weight of 55 kD on sodium dodecylsulfate polyacrylamide gel electrophoresis (SDS-PAGE) (p55-TNF-R) and a receptor with an apparent molecular weight of 75 kD on SDS-PAGE (p75-TNF-R).

Both forms of TNF-receptors have been cloned, namely p55-TNF-R by Loetscher et al. [Cell 61, 351–359, (1990)] and p75-TNF-R for example by Dembic et al. [Cytokine 2, 53–58, (1990)] (for both receptors see also European Patent Application No. 90116707.2) and it was found more recently that both receptors bind not only TNF-α but also TNF-β with high affinity [Schönfeld et al., J. Biol. Chem. 266, 3863–3869 (1991)].

It is well known in the art that on the basis of its biological activities TNF-α can be a valuable compound for the treatment of various disorders. For example TNF-α, alone or in combination with interferon, can be an effective antitumor agent [Brouckaert et al., Int. J. Cancer 38, 763–769 (1986)]. However, its systemic toxicity is a major limitation to its wider therapeutic use [Taguchi T. and Sohmura Y., Biotherapy 3, 177–186 (1991)].

Human TNF-α (hTNF-α) and murine TNF-α (mTNF-α) bind with almost equal affinity to human p55-TNF-R and to human p75-TNF-R. It has, however, been shown that in mice human TNF-α (hTNF-α), only binds to the smaller mouse TNF receptor (murine p55-TNF-R). In mice hTNF-α is far less toxic than murine TNF-α (mTNF-α), which binds to both mouse receptors, mp55-TNF-R and mp75-TNF-R. For example, in C57B16 mice, the LD50 is about 10 μg/mouse and 500 μg/mouse with mTNF-α and hTNF-α, respectively [Brouckaert et al., Agents and Actions 26, 196–198 (1989); Everaerdt, B. et al., Biochem. Biophys. Res. Comm. 163, 378–385 (1989); Lewis, M. et al., Proc. Natl. Acad. Sci. USA 88, 2830 (1991); Brouckaert, P., Libert, C., Everaerdt, B. and Fiers, W. (1992). "Selective species specificity of tumor necrosis factor for toxicity in the mouse." Lymphokine Cytokine Res. 11, 193–196]. Hence it was proposed that the p75-TNF-R plays a special role in systemic toxicity.

It also has been reported that proliferative signals can be mediated by hp75-TNF-R in human T lymphocytes (Gehr et al., J. Immunol. 149, 911, 1992; Tartaglia et al., Proc. Natl. Acad. Sci. USA 88, 9292, 1991).

Human Tumor Necrosis Factor muteins, showing a significant difference between their binding affinity to the human p75-Tumor-Necrosis-Factor-Receptor (hp75-TNF-R) and to the human p55-Tumor-Necrosis-Factor-Receptor (hp55-TNF-R), have been described in European Patent Application Publication Nos. 486 908, and 563 714 where hTNF muteins are disclosed which have retained binding activity to hp55-TNF-R, but have lost nearly all binding to hp75-TNF-R.

SUMMARY OF THE INVENTION

This invention is directed to a human TNFα mutein which binds to the hp75-TNF-R with higher binding affinity than to the hp55-TNF-R. This mutein has the sequence of wild-type human TNF α, except that at least one amino acid in the wild-type sequence has been substituted in the claimed mutein with a different amino acid. The different amino acids of the mutein occur at one or more of the positions 33, 65, 67, 75, 143, 144, 145, 146, and 147 of wild-type human TNF α. Pharmaceutically acceptable salts of the muteins of this invention are also part of the invention.

Higher binding affinity means that the muteins of this invention bind to hp75-TNF-R more strongly than they bind to hp55-TNF-R, by any conventional binding assay. In addition, the muteins bind at most 20 times, preferably not more than 10 times less strongly to hp75-TNF-R than does wild-type human TNF α and bind more than 10 times, preferably more than hundred times, less strongly to hp55-TNF-R than does wild-type human TNF α, as measured by any conventional binding or competitive binding assay.

The muteins of this invention bind to hp75-TNF-R with higher affinity than to hp55-TNF-R because of the different amino acid or acids at the sequence positions described, and in addition need not be exactly homologous to wild-type human TNF α at other positions in the sequence. A mutein which has a different amino acid at position 143, 145, or both is preferred.

The muteins of this invention are potentially useful in the same areas in which TNF and other cytokines are useful. In addition, the preferential binding of the muteins to hp75-TNF-R is useful to select properties conferred by activation of hp-TNF-R and to reduce undesired effects of activation of both hp75-TNF-R and hp55-TNF-R or activation of hp55-TNF-R alone.

BRIEF DESCRIPTION OF THE FIGURES

Abbreviations and symbols used are: B, E, H, S, Xb and X which indicate cleavage sites for restriction enzymes BglI, EcoRI, HindIII, SalI, XbaI and XhoI, respectively.

▭, represents the regulatable promoter/operator element N250PSN25OP29, ▦ represents the synthetic ribosomal binding site RBSII,SphI, ▶ represents genes for TNFα (TNFα), β-lactamase (bla), chloramphenicol acetyltransferase (cat), lac repressor (lacI) and neomycin phosphotransferase (neo), ▥ represents transcriptional terminators $t_o$ of phage lambda ($t_o$) and T1 of the *E. coli* rrnB operon (T1)⇌represents the replication regions of plasmids pBR322 and pREP4 (repl.),→represents the coding region under control of N250PSN250P29 and RBSII,SphI.

amino acid sequence shown represents in the three letter code the sequence of the mature human TNFα (157 amino acids;

SEQ ID No. 1 and 2).

Figure 2A:
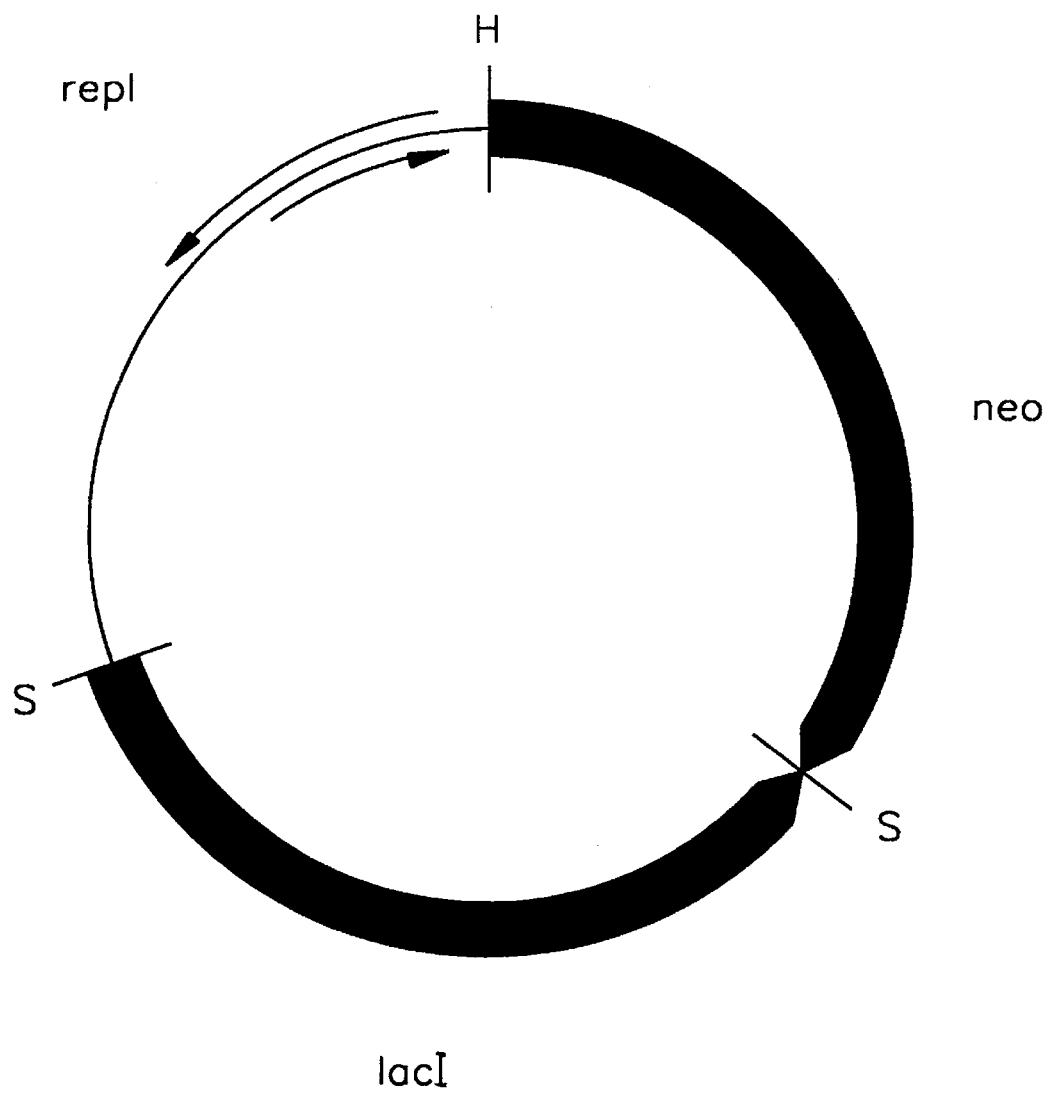

FIG. 2A is a schematic drawing of the plasmid pREP4.

FIG. 2B/1–2B/4 displays the complete nucleotide sequence of plasmid pREP4 (SEQ ID No. 3). In this sequence, the recognition sequences of the restriction enzymes depicted in FIG. 2a are indicated (see also FIGS. 2b/1–2b/3 of EP 486 908).

Figure 3:
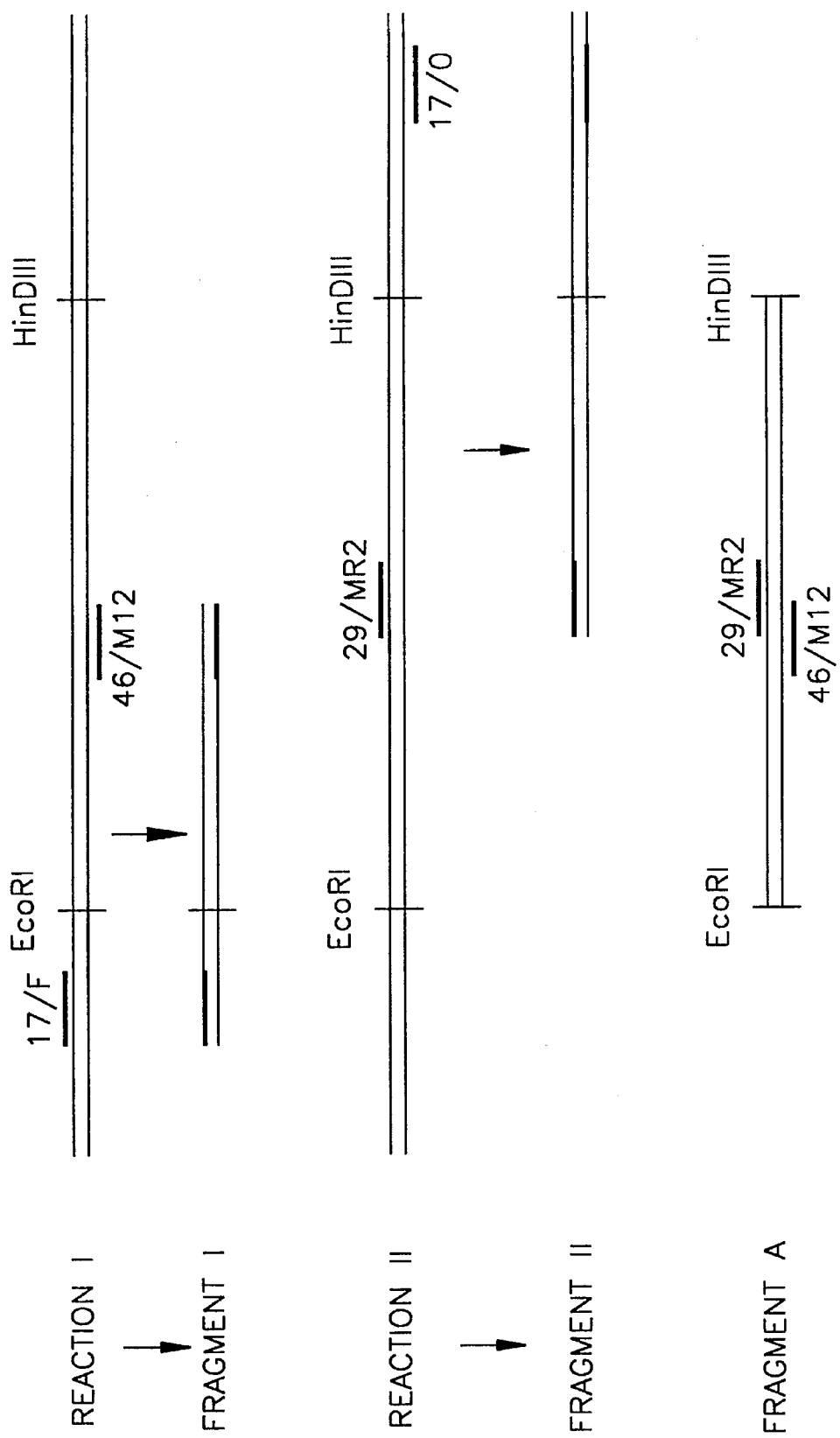

FIG. 3 outlines the preparation of an EcoRI-HindIII fragment encoding the TNFα mutein TNFα (D143N, A145R).

Figure 4A:
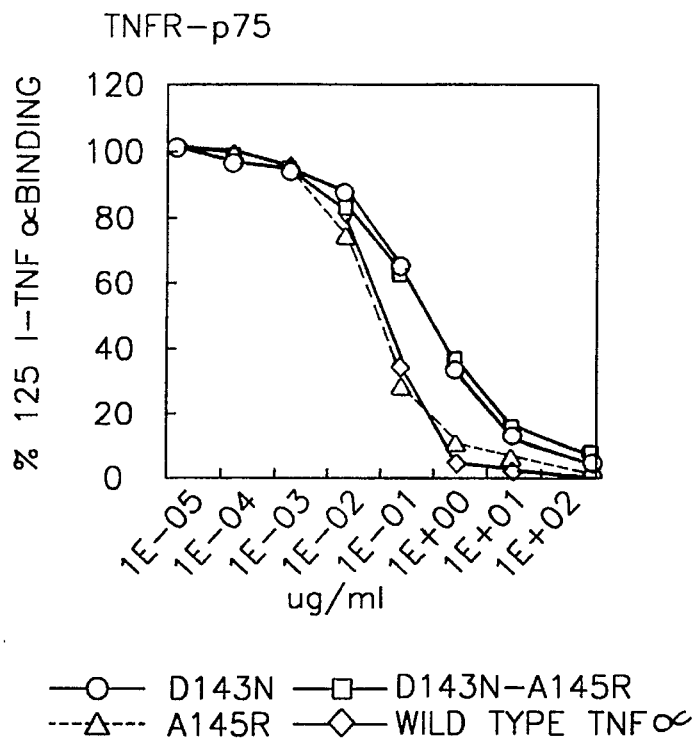
Figure 4B:
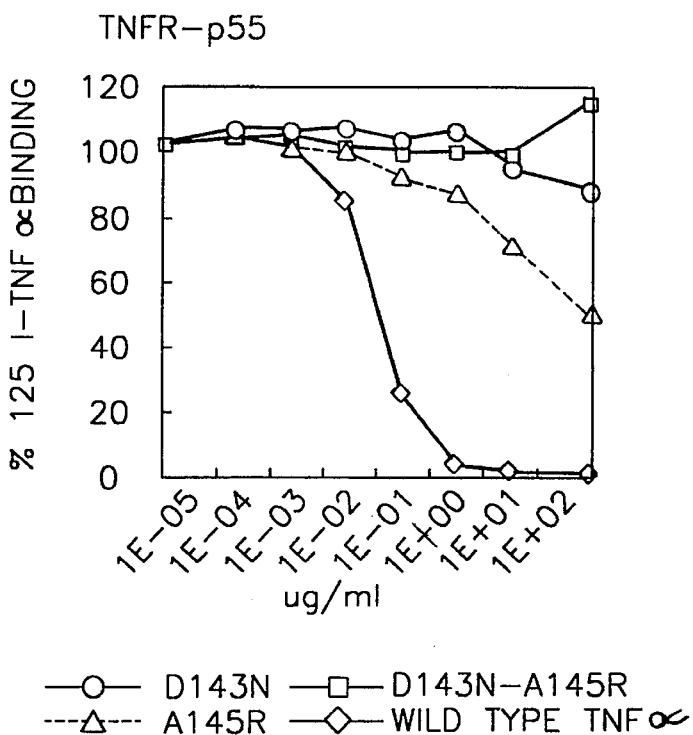

FIG. 4 illustrates the Competitive binding of Human Wild-type TNFα and D143N, A145R and D143N-A145R Muteins to Human TNFR-p75 and TNFR-p55. 96 well microtiter plates coated with recombinant human TNFR-p75-hγ3 fusion protein (upper panel) and recombinant human TNFR-p55-hγ3 fusion protein (lower panel) were incubated with radiolabelled human TNFα in the presence of different concentrations of unlabelled wild-type TNFα, D143N, A145R or D143N-A145R muteins. After three hours at room temperature bound radioactivity was counted in a γ-counter.

DETAILED DESCRIPTION OF THE INVENTION

The present invention provides a human Tumor Necrosis Factor mutein having higher binding affinity for human p75-Tumor-Necrosis-Factor-Receptor than for human p55 Tumor-Necrosis-Factor-Receptor (the term "human Tumor Necrosis Factor Mutein" when used herein includes pharmaceutically acceptable human Tumor Necrosis Factor Mutein salts).

The amino acid sequence of (wild-type) human TNF-α as disclosed by Pennica et al. [see above] is as follows:

| 1 | | | | | | | | | 10 | | | | |
|---|---|---|---|---|---|---|---|---|---|---|---|---|---|
| VAL | ARG | SER | SER | SER | ARG | THR | PRO | SER | ASP | LYS | PRO | VAL | ALA | HIS |
| | | | | 20 | | | | | | | | | | 30 |
| VAL | VAL | ALA | ASN | PRO | GLN | ALA | GLU | GLY | GLN | LEU | GLN | TRP | LEU | ASN |
| | | | | | | | | | 40 | | | | | |
| ARG | ARG | ALA | ASN | ALA | LEU | LEU | ALA | ASN | GLY | VAL | GLU | LEU | ARG | ASP |
| | | | | 50 | | | | | | | | | | 60 |
| ASN | GLN | LEU | VAL | VAL | PRO | SER | GLU | GLY | LEU | TYR | LEU | ILE | TYR | SER |
| | | | | | | | | | 70 | | | | | |
| GLN | VAL | LEU | PHE | LYS | GLY | GLN | GLY | CYS | PRO | SER | THR | HIS | VAL | LEU |
| | | | | 80 | | | | | | | | | | 90 |
| LEU | THR | HIS | THR | ILE | SER | ARG | ILE | ALA | VAL | SER | TYR | GLN | THR | LYS |
| | | | | | | | | | 100 | | | | | |
| VAL | ASN | LEU | LEU | SER | ALA | ILE | LYS | SER | PRO | CYS | GLN | ARG | GLU | THR |
| | | | | 110 | | | | | | | | | | 120 |
| PRO | GLU | GLY | ALA | GLU | ALA | LYS | PRO | TRP | TYR | GLU | PRO | ILE | TYR | LEU |
| | | | | | | | | | 130 | | | | | |
| GLY | GLY | VAL | PHE | GLN | LEU | GLU | LYS | GLY | ASP | ARG | LEU | SER | ALA | GLU |
| | | | | 140 | | | | | | | | | | 150 |
| ILE | ASN | ARG | PRO | ASP | TYR | LEU | ASP | PHE | ALA | GLU | SER | GLY | GLN | VAL |
| | | | | | | 157 | | | | | | | | |
| TYR | PHE | GLY | ILE | ILE | ALA | LEU | [SEQ ID:2] | | | | | | | |

Figure 1A:
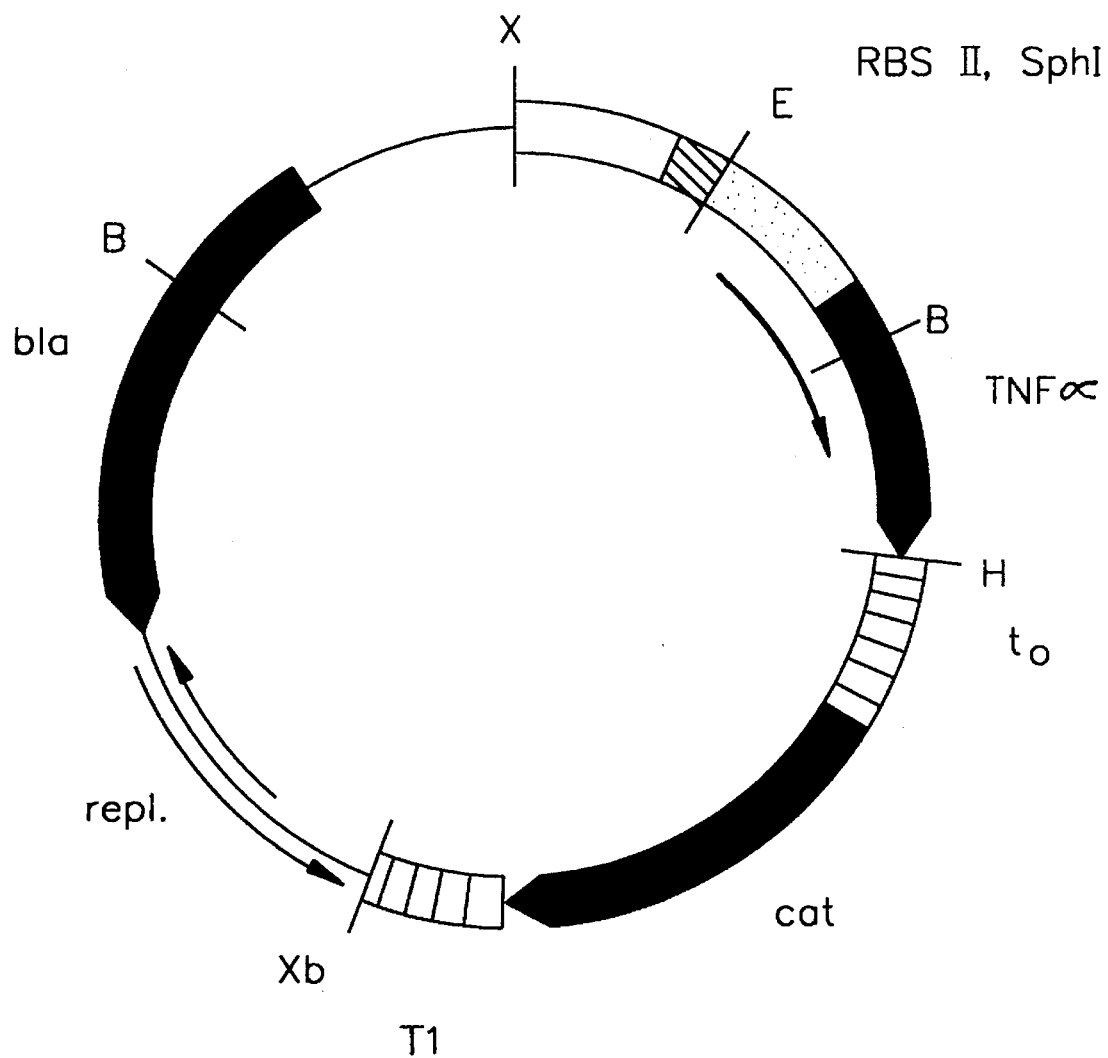

FIG. 1A is a schematic drawing of the plasmid pDS56/RBSII,SphI-TNFα.

FIG. 1B/1–1B/4 displays the complete nucleotide sequence of plasmid pDS56/RBSII,SphI-TNFα (SEQ ID No. 1). In this sequence, the recognition sequences of the restriction enzymes depicted in FIG. 1a are indicated. The or as disclosed by Marmenout et al. (see above) or Wang et al. (see above) or Shirai et al. or more specifically as coded for by the nucleotide sequence of the insert of the plasmid pDS56/RBSII,SphI-TNFα (SEQ ID No. 1; see FIGS. 1a and 1b and Example I; or FIGS. 3b1–3b3 of EP 486 908) coding for mature TNF-α.

Prior to the present invention there was no indication that hTNF muteins could be prepared which bind selectively to hp75TNF-R. Muteins according to the present invention can advantageously be used to characterise hp75-TNF-R and also have potential beneficial diagnostic and therapeutic applications.

Preferably the mutein comprises at least one amino acid change relative to wild-type human TNF-α [SEQ ID: 2] at a position corresponding to position 33, 34, 65, 67, 75, 143, 145 and/or 147 of the wild-type sequence, when measured relative to the N-terminal amino acid. The term "corresponding to" is used herein to indicate that the muteins of the present invention need not be exactly homologous with wild-type human TNF-α at positions other than those indicated above, since at such positions deletions, insertions or substitutions are contemplated relative to the wild-type amino-acid sequence, provided that these have no substantial effect on binding affinity to hp75-TNF-R.

Amino acid substitutions in proteins and polypeptides which do not essentially alter biological activity are known in the art and described, e.g. by H. Neurath and R. L. Hill in "The Proteins", Academic Press, New York (1979), in particular in FIG. 6 of page 14. The most frequently observed amino acid substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly and vice versa.

Preferably the mutein comprises at least one of the following amino acid changes at a position corresponding to the position indicated for the wild-type sequence [SEQ ID: 2]:

A33T
K65A
K65W
Q67K
Q67T
Q67Y
L75H
L75W
D143N
D143E
D143F
D143W
D143Y
D143V
D143V-F144L-A145S
D143N-A145R
D143V-A145S
A145R
A145D
A145G
A145H
A145K
A145F
A145S
A145T
A145W
A145Y
A145V
E146R
S147L

The above muteins are human TNF α muteins which have a higher binding affinity for hp75-TNF-R than for hp55-TNF-R, and comprise the sequence of wild-type human TNF α except at least one amino acid in that sequence is a different amino acid at the position corresponding to the position indicated for the sequence of wild-type human TNF α [SEQ ID: 2]. The different amino acids are as listed above.

In this nomenclature the letters used represent amino acids, based upon the single letter amino acid code. Dashes are used to separate amino acid changes at more than one position. For each amino acid change indicated, the first letter refers to the amino acid in wild-type human TNF-α [SEQ ID: 2] while the second letter indicates the corresponding amino acid in the mutein. The numbers used indicate the positions in the wild-type sequence at which the amino acids indicated for the wild-type sequence occur.

Of these variants, those listed below are preferred, having been found to have particularly good binding selectivity for hp75-TNF-R. Preferred examples of the above muteins in addition further comprise at least one of the following amino acids at the position corresponding to the position indicated for the sequence of wild-type human TNF α[SEQ ID: 2], as follows:

K65W
D143N
D143E
D143F
D143W
D143Y
D143V
k5 D143V-F144L-A145S
D143N-A145R
D143V-A145S
A145R
A145H
A145K
A145F
A145W
A145Y

Examples of the above preferred muteins in addition further comprise at least one of the following different amino acids at the position corresponding to the position indicated for the sequence of wild-type human TNF α[SEQ ID: 2]. The different amino acids for these particularly preferred variants are those listed below:

D143N
D143E
D143F
D143W
D143Y
D143V
D143V-F144L-A145S
D143N-A145R
D143V-A145S
A145R
A145K
A145F
A145W
A145Y

One of the above muteins in addition further comprises at least one of these following different amino acids at the position corresponding to the position indicated for the sequence of wild-type human TNF α [SEQ ID: 2]:

D 143N

D 143Y

A 145F

A 145R

A 145W

D 143 N-A 145 R

Also part of this invention are muteins as described which bind to the hp75-TNF-R with higher affinity than to hp55-TNF-R, and which comprise the sequence of wild-type human TNF α [SEQ ID: 2] with specific different amino acids at positions 33, 65, 67, 75, 143, 144, 145, 146, and 147. The different amino acid at position 33 is T, at position 65 is A or W, at position 67 is K, T, or Y, at position 75 is H or W, at position 143 is N, E, F, W, Y, or V, at position 145 is R, D, G, H, K, F, S, T, W, Y, or V, at 146 is R, and at 147 is L.

In one example of the above mutein when the different amino acid at position 143 is V, the different amino acid at position 145 is S. In another example, N is at position 143 and R is at position 145. In a further example the amino acid at position 144 is L.

In additional examples of the above mutein, the different amino acid at position 143 is N, E, F, W, Y, or V and the different amino acid at position 145 is R, H, K, F, W, or Y. This mutein may have W at position 65 and R, K, F, W, or Y at position 145. The latter mutein may have N or Y at position 143 and F, R, or W at position 145.

It is notable that all of these latter alternatives have amino acid changes at positions corresponding to positions 143 and/or 145 of the wild-type sequence [SEQ ID: 2]. Changes at these positions are therefore preferred.

The hTNF muteins of the present invention may additionally contain sequences of several amino acids which are coded for by "linker" sequences. These sequences may arise as a result of the expression vectors used for expression of the hTNF muteins as defined above.

The hTNF muteins of the present invention can also contain specific sequences that bind with high selectivity to an affinity carrier material so as to aid purification. Examples of such sequences are sequences containing at least two adjacent histidine residues (see in this respect European Patent Application, Publication No. 282 042). Such sequences bind selectively to nitrilotriacetic acid nickel chelate resins (Hochuli and Döbeli, Biol. Chem. Hoppe-Seyler 368, 748 (1987); European Patent Application, Publication No. 253 303). hTNF muteins which contain such a specific sequence can be linked either to the C-terminus or the N-terminus, or to both termini, of the hTNF-mutein amino acid sequences.

The hTNF muteins of the present invention can also be combined with different immunoglobulin heavy chain or light chain polypeptides. This leads to chimetic hTNF mutein immunoglobulin polypeptides which could have increased half-life in vivo. Increased half-life in vivo has been shown, e.g., for chimeric polypeptides consisting of the first two domains of the constant regions of the heavy chain or the light chain of a mammalian immunoglobulin (see Traunecker et al., Nature 331, 84–86 [1988] and European Patent Application, Publication No. 394 827). Chimeric proteins of hTNF muteins fused to any other peptide sequence are also possible.

The hTNF muteins can also be coupled to polymers, e.g. polyethylene glycol or polypropylene glycol having a molecular weight of 500 to 20,000 daltons (pegylated hTNF-muteins). This leads to protected hTNF mutein compositions which could be substantially non-immunogenic. Several modes of coupling the polymer with the polypeptide are available and described, e.g., in U.S. Pat. No. 4,179,337. Accordingly a pegylated hTNF-mutein or a pharmaceutically acceptable salt thereof is also an object of the present invention. Therefore, any of the muteins described herein can be coupled or linked to a polyalkylene glycol molecule to form a compound which is part of this invention. Polyalkylene includes the polymers above, and also branched or substituted alkylene structures as part of the polymer. More than one polyalkylene glycol may be linked to a mutein, in any combination. As noted above conventional coupling means any conventional means of attaching a polyalkylene glycol to a polypeptide, preferably by a covalent link. The coupling may be direct or may use linkers between the polymer and the mutein.

The hTNF muteins of the present invention can be produced by methods known in the art and described e.g. in Sambrook et al. [Molecular Cloning, A Laboratory Manual, 2nd ed., Cold Spring Harbour Laboratory, Cold Spring Harbour Laboratory Press, USA (1989)]or e.g. in the following paragraphs. Whether such hTNF muteins still show selective binding affinity for the p75-TNF-R can be determined as described in the following Examples. Alternatively, the hTNF muteins of the present invention can also be chemically synthesized using standard methods known in the art, preferably solid state methods, such as the methods of Merrifield (J. Am. Chem. Soc. 85, 2149–2154 [1963]). Furthermore pharmaceutically acceptable salts of such muteins are also an object of the present invention. Such salts can be produced by methods known in the art.

Beneficial and unwanted TNF-α activities may be obtained and distinguished by, using compounds specifically binding to one or the other TNF-receptor, such as the hTNF muteins of the present invention. These activities may be useful to treat disease states where TNF plays a role.

DNA-sequences coding for hTNF-muteins as hereinbefore described are also an object of the present invention. In addition to their function as an intermediate for obtaining the muteins of the present invention, such sequences (or fragments thereof) can be used in gene therapy, whereby an existing gene can be modified to give beneficial effects. The sequences (or fragments thereof) can also be used as antisense DNA for the regulation of gene expression by binding to complementary mRNA sequences. Gene therapy and antisense techniques are known in the art.

Such DNA-sequences can be constructed starting from genomic- or cDNA-sequences coding for hTNF as disclosed in the art [see above] using known methods of in vitro mutagenesis [see e.g. Sambrook et al., 1989]. RNA sequences complementary to the DNA sequences of the present invention are also within the scope of the present invention and are of utility e.g. for the preparation of cDNA sequences.

The mutagenesis referred to above can be carried out at random in order to obtain a large number of mutants which can then be tested for their desired properties in appropriate assay systems or, in order to mutate defined positions in a given DNA-sequence, by so called site directed mutagenesis [see e.g. Sambrook et al., 1989, 15.51–15.113] or by mutagenesis using the polymerase chain reaction [see e.g. White et al., Trends in Genetics 5, 185–189 (1989)]. Any other conventional mutagenesis method may be used.

One chemical mutagen which is often used for mutagenesis at random is sodium bisulfite which converts a cytosine residue into an uracil residue and hence leads to a transition of "C" to "T" (standard abbreviations for nucleotides) [for the method see e.g. Shortle and Nathans, Procd. Nat. Acad. Sci. U.S.A. 75, 2170–2174 (1978) or Pine and Huang, Meth. Enzym. 154, 415–430 (1987)]. This mutagen acts solely on single stranded DNA whereas the expression of the mutated target DNA sequence is achieved with a double stranded plasmid vector. One possibility to avoid the necessity of recloning in mutagenesis and expression vectors is the use of so called "phasmids". These are vectors which, in addition to a plasmid origin of replication, carry also an origin of replication derived from a filamentous phage. Examples of such phasmids are the pMa-and pMc-phasmids as described by Stanssen et al. [Nucleic Acids Res. 17, 4441–4454, (1989)]. Using this expression system one can construct so called "gap-duplex"-structures [see also Kramer et al., Nucl. Acids. Res. 12, 9441–9456 (1984)] where only the TNF-coding sequence (see above) is in a single stranded configuration and therefore accessible for the specific chemical mutagen. "gap-duplexes" to be used in adrandom mutagenesis can be constructed as described for site-specific mutagenesis by Stanssen et al. [see above] with the exception that the (−)strand contains the same active antibiotic resistance gene as the (+)strand. By making use of different restriction sites in the DNA-sequence encoding hTNFα, variation of the width of the gap is possible. Examples of such restriction sites are the Cla1-Sal1 sites (470 nucleotides), BstX1-BstX1 sites (237 nucleotides) or Sty1-Sty1 sites (68 nucleotides). Such gap-duplex-constructs can then be treated with increasing concentrations (up to 4M) of bisulfite, followed by several dialysis steps, as described by Shortle and Nathans (see above). A suitable procaryotic host cell can then be transformed by such phasmid constructs according to methods known in the art and described e.g. by Sambrook et al. (see above). A suitable procaryotic host cell means in this context a host cell deficient in a specific repair function so that an uracil residue is maintained in the DNA during replication and which host cell is capable of expressing the corresponding mutated TNF. Such specific host strains are known in the art, for example for *E. coli* strains, e.g. *E. coli* BW 313 [Kunkel, T. A., Procd. Natl. Acad. Sci. USA 82, 488–492 (1985)]. The resulting clones can then be screened for those expressing a desired hTNF mutein by appropriate assay systems. For example each colony can be inoculated in a microtiterplate in a suitable medium containing the relevant antibiotic. The cells may be lysed by addition of lysozyme, followed by sequential freeze-thaw cycles. After precipitation of nucleic acids and centrifugation, the supernatant of each colony can directly be used in appropriate assays as described, e.g., in Example III of the present specification.

If desired, the specific sites of mutation can be determined, for example by restriction fragment analysis [see e.g. Sambrook et al. (see above)]. By determination of the DNA-sequence of such fragments the exact position of the mutation can be determined and if such mutation leads to an amino acid replacement the new amino acid can be derived from the determined DNA-sequence. DNA-sequencing can be performed according to methods known in the art, e.g. by using T7 polymerase on supercoiled DNA with a commercially available sequencing kit (Pharmacia, Uppsala, Sweden).

As already mentioned above, another method of mutating a given DNA-sequence is by "site directed mutagenesis". A widely used strategy for such kind of mutagenesis as originally outlined by Hutchinson and Edgell [J. Virol. 8, 181 (1971)] involves the annealing of a synthetic oligonucleotide carrying the desired nucleotide substitution to a target region of a single-stranded DNA-sequence wherein the mutation should be introduced [for review see Smith, Annual. Rev. Genet. 19, 423 (1985) and for improved methods see references 2–6 in Stanssen et al. (1989)].

One such preferred method is the one of Stanssen et al. (1989) using "gapped duplex DNA" as originally described by Kramer et al. (1984) [see above and Kramer and Fritz, Methods in Enzymology, (1987), Academic Press, Inc., USA] but using antibiotic resistance genes instead of M13 functional genes for selection of the mutation containing strand in addition with the phasmid-technology as also described by Stanssen et al. (1989) [see above]. An advantage of this method lies also in the capability of performing successive cycles of mutagenesis without the need to transfer the gene to a new mutagenesis vector: second round mutagenesis differs only in the selection to another antibiotic marker (Stranssen et al., see above). As a control site-specific back mutagenesis of the mutant to the wild-type TNF can be used. In addition, the use of an oligonucleotide, creating or destroying a restriction site in the TNF gene, allows to control the mutant not only by hybridization to the oligonucleotide used for site directed mutagenesis but also by the presence or absence of the restriction site. In order to create a set of hTNF muteins wherein at a defined position of their amino acid sequence the wild-type amino acid is replaced by any naturally occurring amino acid a set of oligonucleotides is used with all possible codons at the defined position.

As already mentioned above, another possibility of mutating a given DNA-sequence is the mutagenesis by using the polymerase chain reaction (PCR). The principles of this method are outlined e.g. by White et al. (1989), whereas improved methods are described e.g. in Innis et al. [PCR Protocols: A Guide to Methods and Applications, Academic Press, Inc. (1990)].

PCR is an in vitro method for producing large amounts of a o specific DNA fragment of defined length and sequence from small amounts of a template DNA. Thereby, PCR is based on the enzymatic amplification of the DNA fragment which is flanked by two oligonucleotide primers that hybridize to opposite strands of the target sequence. The primers are oriented with their 3' ends pointing as towards each other. Repeated cycles of heat denaturation of the template, annealing of the primers to their complementary sequences and extension of the annealed primers with a DNA polymerase result in the amplification of the segment between the 5' ends of the PCR primers. Since the extension product of each primer can serve as a template for the other, each cycle essentially doubles the amount of the DNA fragment produced in the previous cycle. Since the primers are physically incorporated into the amplified product and mismatches between the 5' end of the primer and the template do not significantly affect the efficiency of the amplification, it is possible to alter the amplified sequence thereby introducing the desired mutation into the amplified DNA. By utilizing the thermostable Taq DNA polymerase isolated from the thermophilic bacteria Thermus aquaticus, it has been possible to avoid denaturation of the polymerase which necessitated the m addition of enzyme after each heat denaturation step. This development has led to the automation of PCR by a variety of simple temperature-cycling devices. In addition, the specificity of the amplification reaction is increased by allowing the use of higher temperatures for primer annealing and extension. The increased specificity improves the overall yield of amplified products by minimizing the competition by non-target fragments for enzyme and primers.

Design and synthesis of oligonucleotides can be effected as known in the art and described e.g. in Sambrook et al. (1989) or in one of the references cited above with respect to site directed mutagenesis.

As soon as a DNA-sequence coding for a hTNF-mutein of the present invention has been created, expression can be effected by the phasmid technology as described above or by use of any suitable pro-or eukaryotic expression systems well known in the art [see e.g. Sambrook et al., see above].

Expression by known methods is effected preferably in any conventional prokaryotic cells, for example, in *E. coli*, *Bacillus subtilis* and so on, whereby *E. coli*, specifically *E. coli* K12 strains e.g. M15 [described as DZ 291 by Villarejo et al. in J. Bacteriol. 120, 466–474 (1974)], HB 101 [ATCC No. 33694], WK6 (Stranssens et al. see above) or *E. coli* SG13009 [Gottesman et al., J. Bacteriol. 148, 265–273 (1981)] are preferred. Expression of the hTNF muteins of the present invention can also be effected in any conventional lower or higher eukaryotic cell, for example yeast cells (like Saccharomyces, Pichia etc.), filamentous fungi (like Aspergillus etc.) or cell lines (like chinese hamster ovary cell lines etc.), whereby expression in yeast cells is preferred [see Sreekrishna et al., Biochem. 28, 4117–4125, (1989); Hitzeman et al., Nature 293, 717–722 (1981); European Patent Application Publication No. 263 311]. Expression of the hTNF muteins of the present invention may occur in such systems either intracellularly, or, after suitable adaption of the gene, extracellularly (see Leemans et al., Gene 85, 99–108, 1989).

Suitable vectors used for expression in E. coli are mentioned e.g. by Sambrook et al. [see above] or by Fiers et al. in "Procd. 8th Int. Biotechnology Symposium" [Soc. Franc. de Microbiol., Paris, (Durand et al., eds.), pp. 680–697 (1988)] or and more specifically vectors of the pDS family [Bujard et al., Methods in Enzymology, eds. Wu and Grossmann, Academic Press, Inc. Vol. 155, 416–433 (1987); Stüber et al., Immunological Methods, eds. Lefkovits and Pernis, Academic Press, Inc., Vol. IV, 121–152 (1990)] like for example pDS56/RBSII,SphI-TNFα (D143N, A145R) (see Example I) or pDS56/RBSII,SphI-TNFα (mutein) (see Example II), where the term "mutein" represents the TNFα muteins listed in Table 1. Since with these specific pDS56/RBSII-plasmids, due to their specific regulatable promoter/operator elements and ribosomal binding sites, a high level of expression can be achieved, the plasmids can be maintained in *E. coli* cells only when the activity of the promoter/operator element is repressed by the binding of a lac repressor to the operator. The activity of the promoter can be restored at the desired cell density by addition of IPTG, which inactivates the repressor and clears the promoter. Since most of the *E. coli* strains do not provide enough repressor molecules to completely repress the function of the promoter sequences present in these high copy number plasmids, such *E. coli* strains, like *E. coli* M15 or SG13009, have to be transformed at first with a plasmid, like pREP 4 [SEQ ID: 3] (see FIGS. 2a and b), coding for the lac repressor, before being transformed with the specific pDS56/RBSII-plasmids of the invention which can then be stably maintained in the *E. coli* cells. Beside coding for the lac repressor, pREP4 contains also a region of the plasmid pACYC184 [Chang and Cohen, J. Bacteriol. 134, 1141–1156 (1978)], which contains all information required for replication and stable transmission to daughter cells [for additional information see also "System for high level production in *E. coli* and rapid purification of recombinant proteins: application to epitope mapping, preparation of antibodies and structure function analysis" by Stüber et al. in Immunological Methods, Vol. IV, pp 121–152, Lefkovits and Pernis (eds.), Academic Press, New York (1990)].

Transformation of the host cells by vectors as described above may be carried out by any conventional procedure [see for example Sambrook et al. (see above)]. Where the host cell is a prokaryote, such as *E. coli* for example, competent cells which are capable of DNA uptake are prepared from cells harvested after exponential growth phase and subsequently treated according to the known $CaCl_2$-method. Transformation can also be performed after forming a protoplast of the host cell or by other methods known in the art and described, e.g., in Sambrook et al. (see above). Therefore a vector, especially for expression in a prokaryotic or lower eukaryotic host cell, comprising a DNA-sequence coding for an hTNF mutein as described above, and a host cell, especially a prokaryotic host cell, e.g. *E. coli*, or a lower eukaryotic host cell, transformed by such a vector are also an object of the present invention.

Usually, the host organisms which contain a desired expression vector are grown under conditions which are optimal for their growth. In case of a procaryotic host at the end of the exponential growth, when the increase in cell number per unit time decreases, the expression of the desired hTNF mutein is induced, i.e. the DNA coding for the desired hTNF mutein is s transcribed and the transcribed mRNA is translated. The induction can be carried out by adding an inducer or a derepressor to the growth medium or by altering a physical parameter, e.g. a change in temperature. In the expression vectors used in the preferred embodiments of the present invention, the expression is controlled by the lac repressor. By adding isopropyl-β-D-thiogalactopyranoside (IPTG), the expression control sequence is derepressed and the synthesis of the desired hTNF mutein is thereby induced.

The hTNF muteins of the present invention produced by transformed host cells as stated above can be recovered from the culture medium or after opening the cells and/or extraction by any appropriate method known in protein and peptide chemistry such as, for example, precipitation with ammonium sulfate, dialysis, ultrafiltration, gelfiltration or ion-exchange chromatography, gel electrophoresis, isoelectric focusing, affinity chromatography, like immunoaffinity chromatography, HPLC or the like. Specifically preferred methods are precipitation with ammonium sulfate and/or polyethylenimine, dialysis, affinity chromatography, e.g. on phenyl-agarose, specifically phenyl-sepharose, or ion-exchange chromatography, specifically on a MONO-Q- and/or MONO-S-matrix (Pharmacia, Uppsala, Sweden) or more specifically are those as described by Tavernier et al. [J. Mol. Biol. 211, 493–501 (1990)] and those disclosed in Example IV.

It is therefore also an object of the present invention to provide a process for the preparation of hTNF muteins as specified above which process comprises cultivating a transformed host cell as described above, especially a prokaryotic, e.g. *E.coli* or eukaryotic host cell in a suitable medium and isolating a mutein from the culture supernatant or the host cell itself, and if desired pegylating said mutein or preparing a pharmaceutically acceptable salt thereof by methods known in the art. The compounds whenever prepared according to such a process are also an object of the present invention.

The hTNF muteins of the present invention are characterized by showing a selective binding affinity for the human p75-TNF-R. Such property can be determined by any assay known in the art measuring binding affinities. For example the binding of TNF itself and of the muteins of the present invention can be measured using cells in cell culture which express the two types of TNF-receptors to a different degree, like for example Hep-2 cells which exclusively express the human p55-TNF-R and U937 or HL60 cells which express in addition also the human p75-TNF-R [see Brockhaus et al., Procd. Nat. Acad. Sci. U.S.A. 87, 3127–3131, (1990); Hohmann et al., J. Biol. Chem. 264, 14927–14934, (1989); Loetscher et al. (1990); Dembic et al. (1990)]. Of course binding affinities can also be determined directly by using purified native or recombinant p55-TNF-R and p75-TNF-R as specifically described in the Examples, or by using the corresponding soluble analogs of such receptors.

The term selective binding affinity for the human p75-Tumor-Necrosis-Factor-Receptor" refers in the context of the present invention to a difference in binding affinities to the two types of TNF-receptor. The muteins of the present invention thus have a higher binding affinity for hp75-TNF-R than for hp55-TNF-R. This higher binding affinity for hp75-TNF-R is measured by any conventional means. Preferably, with respect to the assay system described in the examples, a mutein of the present invention binds selectively to hp75-TNF-R (desirably to a degree similar to wild-type TNF) but has essentially lost binding to hp55-TNF-R. Desirably, in the context of the assay-system of the Examples, the $K_D$-value [Dissociation-constant; calculated on the basis of the concentrations in the equilibrium of the free mutein and receptor and of the mutein-receptor complex] of a specific hTNF mutein of the present invention is at least a factor of 10 or more, more desirably at least a factor of $10^2$ larger than for wild-type TNF-α determined by using the in vitro binding assay with recombinant soluble hp55-TNF-R, whereas its $K_D$-value determined by using the in vitro binding assay in respect of recombinant soluble hp75-TNF-R for the same hTNF mutein desirably differs not by more than a factor of 20 from that of wild-type TNF-α. It should be understood, however, that these specific $K_D$-values are given for illustration and should not be considered as limiting in any manner.

The hTNF muteins may be administered alone or with one or more additional compounds of the present invention in pharmaceutically acceptable oral, injectable or topical compositions and modes. Administration will be in a dosage such that the amount of the composition in the patient is effective to modify the biological function associated with hTNF mutein function. hTNF muteins may be administered similarly to TNF.

Pharmaceutical compositions containing hTNF muteins in association with a compatible pharmaceutically acceptable carrier material are therefore a further object of the present invention. Any conventional carrier material can be utilized. The carrier material can be an organic or inorganic one suitable for enteral, percutaneous or parenteral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may contain other pharmaceutically active agents. Additional additives such as flavouring agents, preservatives, stabilizers, emulsifying agents, buffers and the like may be added in accordance with accepted practices of pharmaceutical compounding.

The pharmaceutical preparations can be made up in any conventional form including: a) a solid form of oral administration such as tablets, capsules, pills, powders, granules and the like; b) a liquid form for oral administration such as solutions, syrups, suspensions, elixirs and the like; c) preparations for parenteral administration such as sterile solutions, suspensions or emulsions; and d) preparations for topical administrations such as solutions, suspensions, ointments, creams, gels, micronized powders, aerosols and the like. The pharmaceutical preparations may be sterilized and/or may contain adjuvants such as preservatives, stabilizers, wetting agents, emulsifiers, salts for varying the osmotic pressure and/or buffers.

Parenteral dosage forms may be infusions or injectable solutions which can be injected intravenously or intramuscularly. These preparations can also contain other medicinally active substances. Additional additives such as preservatives, stabilizers, emulsifying agents, buffers and the like may be added in accordance with accepted practices of pharmaceutical compounding.

Accordingly it is also an object of the present invention to provide a process for the preparation of a pharmaceutical composition which process is characterized in that a compound obtained by a process of the present invention and if desired, additional pharmaceutically active substances are mixed with a non-toxic, inert, therapeutically compatible carrier material and the mixture is brought into a galenical application form.

Furthermore the use of a compound prepared according to a process of the present invention for the preparation of a pharmaceutical composition as described above is also an object of the present invention.

Finally, antibodies can be raised against the hTNF muteins of the present invention. These antibodies can be used in a well-known manner for diagnostic or therapeutic purposes as well as for purification purposes. Such antibodies can be produced by injecting a mammalian or avian animal with a sufficient amount of a vaccine formulation comprising a hTNF mutein of the present invention and a compatible pharmaceutical carrier to elicit the production of antibodies against said hTNF mutein. The appropriate amount of the hTNF mutein which would be required would be known to one of skill in the art or could be determined by routine experimentation. As used in connection with this invention, the term "pharmaceutical carrier" can mean either the standard compositions which are suitable for human administration or the typical adjuvants employed in animal vaccinations.

As pointed out above, TNF is a potent pleiotropic cytokine. Its many different activities such as, the activation of growth factor for immune cells, mediation in inflammation, or induction of specific genes in endothelium, may be seen in the context of host defense to infection and injury. TNF also exhibits high systemic toxicity; the deleterious effects of bacteriaemia and septic shock or of bacterial meningitis are mediated to a large extent by endogenous cytokines among which TNF has an early and important role. Furthermore, many cells and cell lines are sensitive to a direct cytotoxic activity of TNF. Various systemic effects and cellular toxicity presumably combine in the antitumor activity of TNF seen in animal studies.

These facts form the rational basis for the development of novel therapeutic strategies using the hTNF muteins of the present invention, where in particular the potential to dissect the many different hTNF activities shall be fully exploited to separate unwanted from desired activities by selectively activating only one of the two hTNF receptor types (in contrast to wild-type hTNF which binds and activates both). The potential use of the hTNF muteins of the present invention is not restricted to cancer therapy. Any disease where TNF as host defense factor in bacterial infection [for example Kindler, V. et al., CELL 56, 731–740 (1989); Nakano, Y. et al., J. Immunol. 144, 1935, (1990)] or as mediator in inflammation plays a beneficial role might benefit from a 75kDa TNF receptor type specific drug such as the hTNF muteins of the present invention. Furthermore, TNFα has been shown to have certain catabolic effects on fat cells and on whole animals, and to play a role in cachexia [e.g. Beutler, B. and Cerami, (see above); Hotamisligil et al., Science 259, 87 1993] and TNF muteins of the present invention might be used in treating obesity. It also has been shown that TNFα has a neutralising effect on the insulin-stimulated peripheral glucose utilisation rate [Hotamisligil et al., see above]. Such a putative role of TNFα in obesity-linked insulin resistance might be reconciled with its possible role in cachexia by dose-dependent differences in biological effects and distinct roles of the two TNF receptor systems which might be exploited by receptor-type specific agonists in the presence or absence of wild-type TNF-inhibitors. Even disease states characterised by the toxic activities exerted by excessive TNF release such as septic shock or bacterial meningitis might benefit from TNF receptor specific agonists such as the muteins of the present invention above, alone, or in combination with wild-type TNF antagonists.

A concise summary of the emerging role of TNF for novel therapies, where TNF-Receptor type specific agonists selectively triggering only some of the many different TNF activities may be expected to have significant advantages when compared to wild-type TNF, has been published [Tumor Necrosis Factors, The Molecules and their Emerging Role in Medicine, B. Beutler, ed., Raven Press, 1992, ISBN 0-88167-852-X]. It includes the activities of TNF in modulating endothelial cell homeostatic properties and neutrophil adhesion, tissue ischemia and reperfusion injury, on osteoblasts and osteoclasts in bone resorption, as growth factor on many cells in general and in hematopoiesis, as well as in metabolic and nutritional effects. TNF as a growth/differentiation factor in the generation of lymphokine-activated killer (LAK) cells appears to contribute to the antitumor activities of TNF. Accordingly the use of the hTNF-muteins of the present invention or of pharmaceutically acceptable salts thereof is also an object of the present invention.

All these activities may be enhanced or modulated in combination with other recombinant cytokines such as, for example, interferon-gamma.

The following Examples illustrate details of the invention and are not intended to limit it in any manner, Unless otherwise specified, percentages given below for solids in solid mixtures, liquids in liquids and solids in liquids are on a wt/wt, vol/vol and wt/vol basis, respectively.

EXAMPLE I

Preparation of TNFα(D 143N-A145R)
Plasmid pDS56/RBSII,SphI-TNFα

The human TNFα expression plasmid pDS56/RBSII, SphI-TNFα (see FIG. 1) [SEQ ID: 1] was the source of the TNFα gene for preparation of the various TNFα muteins of this invention. The transformed E. coli strain M15 [pREP4;pDS56/RBSII,SphI-TNFα] has been deposited under the Budapest Treaty for patent purposes at the Deutsche Sammlung von Mikroorganismen und Zellkulturen GmbH (DSM) in Braunschweig, BRD, at Sep. 8, 1991, under the accession number DSM 6713.

Mutagenesis of the TNFα gene using PCR

Two PCR reactions were performed with plasmid pDS56/RBSII,SphI-TNFα (FIG. 1) as the template DNA using a Perkin-Elmer Cetus GeneAmp™ DNA Amplification Reagent Kit with AmpliTaq™ Recombinant Taq DNA Polymerase [see FIG. 3].

Reaction I was performed with primers 17/F [5'-GGCG-TATCACGAGGCCCTTTCG-3' (SEQ ID No. 4); primer 17/F comprises nucleotides 3949–3970 of plasmid pDS56/RBSII,SphI-TNFα] and 46/M12 [5'-GCGAAAGT TGAGATAGTCGGGCCGATTG-3' (SEQ ID No. 5); primer 46/M12 comprises nucleotides which are complementary to nucleotides 552–525 of plasmid pDS56/RBSII,SphI-TNFα, the mutated bases are underlined].

Reaction II was performed with primers 29/MR2 [5'-GAGTCTGGGCAGGTCTACTTTG-3' (SEQ ID No. 6); primer 29/MR1 comprises nucleotides 553–574 of plasmid pDS56/RBSII,SphI-TNFα]and 17/O [5'-CATTAC TGGATCTATAACAGG-3' (SEQ ID NO. 7); primer 17/O comprises nucleotides which are complementary to nucleotides 748–727 of plasmid pDS56/RBSII,SphI-TNFα].

In a typical experiment, 10 µl template DNA (10 ng), 5 µl each of the two primers (100 pmoles each), 16 µl dNTP's mix (1.25 mM of dATP, dGTP, dCTP, and dTTP), 10 µl 10× reaction buffer (100 mM Tris-HCl pH8.3, 500 mM KCL, 15 mM MgCl₂ and 0.1% gelatin), 1 µl (5 units) AmpliTaq™ DNA polymerase and 53 µl H₂O were mixed in an Eppendorf tube and overlaid with 80 ml mineral oil (Perkin-Elmer Cetus). The tubes were transferred to a DNA thermal cycler (TRIO-Thermoblock, Biometra) and kept for 1 min at 94° C., before 35 cycles of melting the DNA (1 min at 94° C.), annealing the primers (1 min at 50° C.), and extending the primers (3 min at 72° C.) were performed. After additional 2 min at 72° C., the reactions were cooled to room temperature and extracted with chloroform. The DNA present in the aqueous phase was precipitated with ethanol and subjected to electrophoresis in a 6% polyacrylamide gel [Sambrook et al., 1989]. After staining of the DNA with ethidium bromide, fragments I and II (see FIG. 3) were isolated from the gel and purified [Sambrook et al., 1989].

Preparation of a DNA fragment encoding TNFα (D143N-A145R)

Fragments I and II were enzymatically phosphorylated, before they were ligated with each other [Sambrook et al., 1989]. After heat-inactivation of the ligase and digestion with restriction enzymes EcoRI and HindIII, the DNA was subjected to electrophoresis in a 6% polyacrylamide gel. After staining of the DNA with ethidium bromide, the EcoRI-HindIII fragment A [see FIG. 3] was isolated from the gel and purified [see above].

Preparation of a plasmid encoding TNFα (D143N-A145R)

The EcoRI-HindIII fragment A was inserted according to standard methods [Sambrook et al., 1989] into the EcoRI-HindIII opened plasmid pDS56/RBSII,SphI-TNFα generating the plasmid pDS56/RBSII,SphI-TNFα(D143N-A145R). Plasmid DNA was prepared [Birnboim et al., 1979] and the identity of the coding region for the TNFα mutein was confirmed by sequencing the double-stranded DNA [Sambrook et al., 1989].

Production of TNFα (D143N-A145R)

Plasmid pDS56/RBSII,SphI-TNFα(D143A-A145R) was transformed into E. coli M15 cells containing already plasmid pREP4 by standard methods [see above]. Transformed cells were grown at 37° C. in LB medium [Sambrook et al., 1989] containing 100 mg/l ampicillin and 25 mg/l kanamycin. At an optical density at 600 nm of about 0.7 to 1.0 IPTG was added to a final concentration of 2 mM. After additional 2.5 to 5 h at 37° C. the cells were harvested by centrifugation.

EXAMPLE II

Preparation of additional TNFα muteins

The additional TNFα muteins listed in Table I were prepared following the procedure described in detail in Example I for the preparation of TNFα (D143N-A145R). The resulting expression plasmids, which are analogous to plasmid pDS56/RBSII,SphI-TNFα (D143N-A145R), were given the name pDS56/RBSII,SphI-TNFα (mutein), where the term 'mutein' represents the TNFα muteins listed in Table 1. These plasmids contain coding regions for the TNFα muteins, in which codons present in plasmid pDS56/RBSII,SphI-TNFα are replaced by codons encoding the said muteins (see Table 1).

EXAMPLE III

Analysis of Recentor Tyne-Specific Binding Activity of Human TNFα Muteins in *E. coli* Lysates Preparation of *E. coli* Lysates 10 ml suspensions of *E. coli* cells transformed and induced as described in Examples I and II were centrifuged at 4'000 rpm for 10 min and resuspended in 0.9 ml of lysis buffer (10 mM Tris-HCl pH 8.0, 5 mM EDTA, 2 mM PMSF, 10 mM benzamidine, 200 units/ml aprotinine and 0.1 mg/ml lysozyme). After 20 min incubation at room temperature 50 µl of 1M $MgCl_2$, 20 µl of 5 mg/ml DNaseI, 50 µl of 5M NaCl and 50 µl of 10% NP-40 were added and the mixture was further incubated at room temperature for 15 min. 0.5 ml of the lysate clarified by centrifugation at 13'000 rpm for 5 min was subjected to ammonium sulfate precipitation (25%–70% cut). The 70% ammonium sulfat pellet was dissolved in 0.2 ml PBS and analyzed by sodium dodecyl sulfate polyacrylamide gel electrophoresis (SDS-PAGE) to confirm presence and approximate amount of the recombinant proteins.

Solid Phase Radioligand Competition Binding Assay 96 well microtiter plates were coated with recombinant human 2.5 TNFR-p75-hγ3 and TNFR-p55-hγ3 fusion proteins (extracellular portion of the receptor fused to the Fc part of human IgG3) at a concentration of 0.3 µg/ml and 0.1 µg/ml, respectively, in phosphate buffered saline (PBS, 100 µl/well, overnight at 4° C.) [Loetscher, H. et al. J. Biol. Chem. 266, 18324–18329 (1991); Lesslauer, W. et al. Eur. J. Immunol. 21, 2883–2886 (1991)]. After blocking with blocking buffer (50 mM Tris pH 7.4, 140 mM NaCl, 5 mM EDTA, 0.02% $NAN_3$, 1% defatted milk powder) the microtiter plate was washed with PBS and incubated in blocking buffer containing 0.1% defatted milk powder with 10 ng/ml human wild-type $^{125}$I-TNFα and various dilutions of *E. coli* lysates ranging from $10^{-2}$ to $10^{-7}$ (10-fold serial dilutions). TNFα was labelled by the Iodogen method (Pierce Chemical Company) to a specific activity of about 10–30 µCi/µg. The volume was 100 µl/well and each lysate dilution was assayed in duplicate or triplicate. After three hours at room temperature the wells were thoroughly washed with PBS and counted in a γ-counter. The results are given in Table 2 for lysates comprising the muteins indicated therein.

EXAMPLE IV

Purification of Human TNFα Muteins

One liter overnight cultures of *E. coli* cells transformed and induced as described in the Examples I and II were collected by centrifugation and resuspended in 20 ml 50 mM Tris pH 7.2, 200 mM KCl, 50 mM $MgCl_2$, 5% glycerol. The cells were disrupted in a French press at a pressure of 20'000 psi or by sonication in a Branson Sonifier (Model 450, 2×2min at maximal output, on ice). After clarification by centrifugation (70'000×g, 30 min, 4° C.) the samples were dialyzed against 20 mM Tris-HCl pH 9.0 overnight at 4° C. and applied to a Q-Sepharose column (Pharmacia, 2.6×15 cm) equilibrated in the same buffer. Proteins were eluted with a linear NaCl gradient (0 to 400 mM in 20 mM Tris pH 9.0) at a flow rate of 1 ml/min. 5 ml fractions were collected and analyzed for the presence of TNFα muteins by SDS-PAGE. Positive fractions were pooled, dialyzed against 20 mM 2-morpholino-ethanesulfonic acid (MES) pH 6.0 and applied to a MonoS column (HR 5/5, LKB-Pharmacia) equilibrated in 20 mM MES pH 6.0. Proteins were eluted with a linear NaCl gradient (0 to 400 mM in 20 mM MES pH 6.0) at a flow rate of 0.5 ml/min. The various TNFα muteins eluted as electrophoretically pure proteins between 250 mM and 350 mM NaCl. After dialysis against PBS the protein concentration was determined by the BCA Protein Assay (Pierce Chemical Company) using wild-type human TNFα as a standard or by absorbance measurements at 280 nm.

EXAMPLE V

Competitive Binding of Purified Human Wild-type TNFα, and Muteins to Recombinant Human TNFR-p75 and TNFR-p55

For the competitive binding assay using purified muteins microtiter plates were coated with recombinant human TNFR-p75-hγ3 and TNFR-p55-hγ3 fusion proteins as described in Example III. After blocking with blocking buffer (50 mM Tris pH 7.4, 140 mM NaCl, 5 mM EDTA, 0.02% $NAN_3$, 1% defatted milk powder) the microtiter plate was washed with PBS and incubated in blocking buffer containing 0.1% defatted milk powder with 10 ng/ml human wild-type $^{125}$I-TNFα and various concentrations of unlabelled wild-type TNFα or muteins ranging from $10^2$ to $10^{-5}$ µg/ml (10-fold serial dilutions). TNFα was labelled by the Iodogen method (Pierce Chemical Company) to a specific activity of about 10–30 µCi/µg. The volume was 100 µl/well and each concentration was assayed in duplicate or triplicate. After three hours at room temperature the wells were thoroughly washed with PBS and counted in a γ-counter.

The results are given in Table 3 and illustrated in FIG. 4 for the muteins indicated therein.

TABLE 1

| Codons used to encode the new amino acids present in the muteins | |
|---|---|
| Mutein | New Codon |
| N19D | GAC |
| Q21S | TCT |
| L29S[a] | TCC |
| L29S-R32W | TCC—TGG |
| L29S-R32W-S86T | TCC—TGG—ACC |
| L29S-S86T | TCC—ACC |
| N30T | ACC |
| R31E | GAG |
| R31K | AAG |
| R31N-R32T | AAC—ACT |
| R31N-R32T-N34S | AAC—ACT—AGT |
| R31N-R32T-S86T | AAC—ACT—ACC |
| R31E-S86T | GAG—ACC |
| R32W[a] | TGG |
| R32W-S86T | TGG—ACC |
| A33D | GAC |
| A33T | ACC |

TABLE 1-continued

Codons used to encode the new amino acids present in the muteins

| Mutein | New Codon |
|---|---|
| N34R | CGT |
| N34D | GAC |
| N34C | TGT |
| N34Q | CAA |
| N34E | GAA |
| N34G | GGT |
| N34H | CAC |
| N34I | ATT |
| N34M | ATG |
| N34F | TTT |
| N34P | CCT |
| N34T | ACT |
| N34Y | TAT |
| N34Y | TAC |
| N34V | GTT |
| K65A | GCA |
| K65W | TGG |
| Q67K | AAA |
| Q67T | ACA |
| Q67Y | TAC |
| H73Q | CAA |
| H73T | ACT |
| L75R | CGT |
| L75H | CAC |
| L75W | TGG |
| S86D | GAC |
| S86T | ACC |
| Y87Q | CAG |
| Y87Q-Q88Δ | CAG— |
| Y87E | GAA |
| Y87G | GGT |
| Y87L | CTG |
| Y87K | AAA |
| Y87F | TTC |
| Y87T | ACC |
| Y87T-E104G | ACC—GGG |
| N92R | CGT |
| I97K | AAG |
| I97Y | TAC |
| S99A | GCA |
| S99Y | TAC |
| Y115W | TGG |
| D143N | AAC |
| D143E | GAA |
| D143F | TTC |
| D143W | TGG |
| D143Y | TAC |
| D143V | GTC |
| D143V-F144L-A145S | GTC—CTG—TCC |
| D143N-A145R | AAC—CGC |
| D143V-A145S | GTC—TCC |
| F144R | CGT |
| F144D | GAT |
| F144G | GGT |
| F144L | TTG |
| F144W | TGG |
| F144Y | TAC |
| A145R | CGC |
| A145D | GAT |
| A145G | GGT |
| A145H | CAC |
| A145K | AAA |
| A145F | TTT |
| A145S | TCC |
| A145T | ACA |
| A145W | TGG |
| A145Y | TAC |
| A145V | GTT |
| E146R | CGT |
| S147N | AAC |
| S147L | CTG |

[a] the L29S and R32W muteins have been constructed in the laboratory of Dr. W. Fiers, University of Ghent (see also EP 486 908).

TABLE 2

Binding of human TNFα Muteins to TNFR-p55 and TNFR-p75

| Mutein | Dilution of E. coli Lysate for 50% Inhibition of $^{125}$I-TNFα Binding (ID50)[a] | | ID50 TNFR-p55[b] / ID50 TNFR-p75 |
|---|---|---|---|
| | TNFR-p55 -fold | TNFR-p75 -fold | |
| wildtype[c] | 14,260 | 14,140 | 1 |
| N19D | 5,000 | 5,000 | 1 |
| Q21S | 2,500 | 2,500 | 1 |
| L29S[c] | 2,980 | <100 | >29.8 |
| L29S-R32W | 5,000 | <<100 | >>50 |
| L29S-R32W-S86T | 2,500 | <<100 | >>25 |
| L29S-S86T | 200 | <<100 | >>2 |
| N30T | 2,860 | 2,500 | 1.1 |
| R31E[c] | 3,470 | 180 | 19.3 |
| R31K | 3,330 | 3,330 | 1 |
| R31N-R32T[c] | 3,260 | <100 | >32.6 |
| R31N-R32T-N34S | <<100 | <<100 | 1 |
| R31N-R32T-S86T | 500 | <100 | >5 |
| R31E-S86T | 2,000 | <<100 | >>20 |
| R32W[c][e] | 8,780 | <100 | >87.8 |
| R32W-S86T | 3,330 | <<100 | >>33.3 |
| A33D | <100 | <<100 | >1 |
| A33T | 1,110 | 1,250 | 0.9 |
| N34R[d] | <100 | <<100 | >1 |
| N34D | 250 | <100 | >2.5 |
| N34C | 250 | <100 | >2.5 |
| N34Q | <100 | <<100 | >1 |
| N34E | 330 | <<100 | >>3.3 |
| N34G | 330 | <100 | >3.3 |
| N34H | 670 | <100 | >6.7 |
| N34I[d] | 200 | <100 | >2 |
| N34M[d] | <100 | <<100 | >1 |
| N34F[d] | 100 | <100 | >1 |
| N34P | <100 | <<100 | >1 |
| N34T | 1,000 | <100 | >10 |
| N34Y[d] | <100 | <<100 | >1 |
| N34Y[d] | <100 | <<100 | >1 |
| N34V[d] | <100 | <<100 | >1 |
| K65A | 20,000 | 33,330 | 0.6 |
| K65W[d] | 500 | 3,330 | 0.2 |
| Q67K | 25,000 | 50,000 | 0.5 |
| Q67T | 25,000 | 33,330 | 0.75 |
| Q67Y | 20,000 | 33,330 | 0.6 |
| H73Q | 10,000 | 10,000 | 1 |
| H73T | 2,000 | 2,000 | 1 |
| L75R | <100 | <100 | 1 |
| L75H | 1,670 | 2,500 | 0.7 |
| L75W | 220 | 330 | 0.7 |
| S86D | 6,670 | 1,000 | 6.7 |
| S86T | 10,000 | <100 | >100 |
| Y87Q | <<100 | <<100 | 1 |
| Y87Q-Q88Δ | <<100 | <<100 | 1 |
| Y87E | <100 | <<100 | >1 |
| Y87G | <<100 | <<100 | 1 |
| Y87L | <<100 | <<100 | 1 |
| Y87K | <<100 | <<100 | 1 |
| Y87F | 200 | <100 | >2 |
| Y87T | <<100 | <<100 | 1 |
| Y87T-E104G | <100 | <100 | 1 |
| N92R | 5,000 | 1,250 | 4 |
| I97K | 143 | <100 | >1.4 |
| I97Y | 2,500 | 330 | 7.6 |
| S99A | 6,670 | 6,670 | 1 |
| S99Y | <100 | <100 | 1 |
| Y115W | 2,220 | 2,220 | 1 |
| D143N[c] | <<100 | 330 | <<0.3 |
| D143E | <100 | 330 | <0.3 |
| D143F | <<100 | 250 | <<0.4 |
| D143W | <<100 | 100 | <<1 |
| D143Y[c] | <<100 | 1,330 | <<0.08 |
| D143V | <<100 | <100 | <1 |
| D143V-F144L-A145S | <<100 | <100 | <1 |

TABLE 2-continued

Binding of human TNFα Muteins to TNFR-p55 and TNFR-p75

| Mutein | TNFR-p55 -fold | TNFR-p75 -fold | ID50 TNFR-p55[b] / ID50 TNFR-p75 |
|---|---|---|---|
| D143N-A145R[d] | <<100 | 125 | <<0.8 |
| D143V-A145S[c] | <<100 | 200 | <<0.5 |
| F144R | 2,500 | 330 | 7.6 |
| F144D | 5,000 | 330 | 15.2 |
| F144G | 2,500 | 2,000 | 1.2 |
| F144L | 5,000 | 5,000 | 1 |
| F144W | 400 | 180 | 2.2 |
| F144Y | 2,860 | 2,860 | 1 |
| A145R | <100 | 3,330 | <0.03 |
| A145D | 5,000 | 6,670 | 0.7 |
| A145G | 2,500 | 6,670 | 0.4 |
| A145H | 330 | 1,670 | 0.2 |
| A145K | <100 | 1,820 | <0.05 |
| A145F[c] | 240 | 6,000 | 0.04 |
| A145S | 14,290 | 25,000 | 0.6 |
| A145T | 5,000 | 6,670 | 0.7 |
| A145W[d] | <<100 | <100 | <1 |
| A145Y | 1,670 | 11,110 | 0.1 |
| A145V | 1,000 | 2,000 | 0.5 |
| E146R | 6,670 | <100 | >67 |
| S147N | 10,000 | 10,000 | 1 |
| S147L | 2,000 | 3,330 | 0.6 |

Human wildtype TNFα and muteins were expressed in E. coli and extracted by lysis of the bacteria. Selective receptor binding activity of extracted wildtype and mutant TNFα was measured in a solid phase radioligand binding assay. Different dilutions of the E. coli lysates ranging from $10^{-2}$ to $10^{-7}$ (10-fold serial dilutions) were tested for competitive binding inhibition of human wildtype $^{125}$I-TNFα to immobilized human TNFR-p75 and TNFR-p55. ID50's (dilution for 50% inhibition) were determined by plotting binding inhibition versus dilution of the lysate. Since the concentration of the recombinant proteins in the lysates varied between 0.05 and 1 mg/ml as estimated from SDS-PAGE analysis, the absolute ID50 values should not be considered as relevant. Receptor selectivity is indicated by directly comparing the ID50 values of a particular mutein for TNFR-p75 and TNFR-p55.
[a]"<" indicates a value less than that of the figure given (here there was measurable inhibition of $^{125}$I-TNFα binding but without reaching 50% inhibition at the lowest dilution tested of 1:100).
"<<" indicates a value considerably less than that of the figure given (here there was no measurable inhibition at the lowest dilution tested of 1:100).
[b]ratio = 1, no receptor selectivity; ratio > 1, TNFR-p55 selectivity; ratio < 1, TNFR-p75 selectivity;

Muteins of the present invention should have an
$$\frac{\text{ID50 TNFR-p55}}{\text{ID50 TNFR-p75}}$$
value of less than 1. This can be less than 0.5, but is preferably less than or equal to 0.2 (see the muteins of claim 5) and more preferably is less than or equal to 0.1 (see the muteins of claim 6). Where the symbols "<" or "<<" are used in Table 1, the muteins concerned shall, optionally, be considered to be within these ranges.
[c)]for these muteins at least three different lysates have been prepared and assayed; the average ID50's are listed.
[d)]these muteins were only partially soluble under the conditions used to prepare the *E. coli* lysate (although it should be noted that different purification methods could be used resulting in different solubilities); the concentration of soluble mutein in these lysates was estimated by SDS-PAGE analysis to be less than 0.05 mg/ml.
[e)]the L29S and R32W muteins have been constructed in the laboratory of Dr. W. Fiers, University of Ghent (see also EP 486 908).

TABLE 3

Binding of Selected Human TNFα Muteins to Human TNFR-p75 and TNFR-p55

| Mutein | Mutein Concentration for 50% Inhibition of $^{125}$I-TNFα Binding (IC50)[a)] TNFR-p55 ng/ml | TNFR-p75 ng/ml | Decrease in Binding Affinity with Respect to Wildtype[b)] TNFR-p55 -fold | TNFR-p75 -fold |
|---|---|---|---|---|
| D143N | >100,000 | 300 | >2,500 | 6.7 |
| D143Y | >100,000 | 350 | >6,660 | 17.5 |
| A145F | 500 | 30 | 33 | 1.5 |
| A145R | 100,000 | 35 | 2,500 | 0.8 |
| A145W | 10,000 | 100 | 250 | 2.5 |
| D143N-A145R | >>100,000 | 300 | >>2,500 | 6.7 |

Muteins with preferential binding to human TNFR-p75 were selected (see Table 2) and purified to apparent homogeneity by sequential ion exchange chromatography. Selective receptor binding activity of the purified muteins was measured in a solid phase radioligand binding assay. Different mutein concentrations ranging from $10^2$ to $10^{-5}$ μg/ml (10-fold serial dilutions) were tested for competitive binding inhibition of human wildtype $^{125}$I-TNFα (10 ng/ml) to immobilized human TNFR-p75 and TNFR-p55. IC50's (concentration for 50% inhibition) were determined by plotting binding inhibition versus concentration (illustrated in FIG. 1).
[a)]>, indicates measurable binding competition but without reaching 50% at 100 μg/ml; >>, indicates no measurable binding competition at the highest concentration tested (100 μg/ml).
[b)]The decrease in affinity has been calculated by dividing the IC50 values obtained for the muteins by the IC50 values obtained for wildtype TNFα. The IC50 value for wildtype TNFα has been determined in each individual set of experiments and was found to vary between 15 to 45 ng/ml depending on the lot of radioiodinated TNFα.

We claim:

1. A human TNF α mutein having the sequence of wild-type human TNF α [SEQ ID:2] wherein the amino acid at position 143 of said sequence has been changed from aspartic acid to asparagine, and the amino acid at position 145 of said sequence has been changed from alanine to arginine.

2. A human TNF α mutein having the sequence of wild-type human TNF α [SEQ ID:2] wherein the amino acid at position 143 of said sequence has been changed from aspartic acid to aspargine.

3. A human TNF α mutein having the sequence of wild-type human TNF α [SEQ ID:2] wherein the amino acid at position 145 of said sequence has been changed from alanine to arginine.

4. A human TNF α mutein having the sequence of wild-type human TNF α [SEQ ID:2] wherein the amino acid at position 145 of said sequence has been changed from alanine to phenylalanine.

5. A human TNF α mutein having the sequence of wild-type human TNF α [SEQ ID:2] wherein the amino acid at position 145 of said sequence has been changed from alanine to tryptophan.

6. A compound which is the mutein of claim 1 linked to a polyalkylene glycol molecule.

7. A compound which is the mutein of claim 2 linked to a polyalkylene glycol molecule.

8. A compound which is the mutein of claim 3 linked to a polyalkylene glycol molecule.

9. A compound which is the mutein of claim 4 linked to a polyalkylene glycol molecule.

10. A compound which is the mutein of claim 5 linked to a polyalkylene glycol molecule.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
 ( A ) LENGTH: 3977 base pairs
 ( B ) TYPE: nucleic acid
 ( C ) STRANDEDNESS: single
 ( D ) TOPOLOGY: circular ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
 ( A ) ORGANISM: plasmid pDS56/RBSII,SphI-TNFalpha ( i x ) FEATURE:
 ( A ) NAME/KEY: CDS
 ( B ) LOCATION: 118..591

( x i ) SEQUENCE DESCRIPTION: SEQ ID NO:1:

```
CTCGAGAAAT CATAAAAAAT TTATTTGCTT TGTGAGCGGA TAACAATTAT AATAGATTCA      60

ATTGTGAGCG GATAACAATT TCACACAGAA TTCATTAAAG AGGAGAAATT AAGCATG        117

GTC AGA TCA TCT TCT CGA ACC CCG AGT GAC AAG CCT GTA GCC CAT GTT       165
Val Arg Ser Ser Ser Arg Thr Pro Ser Asp Lys Pro Val Ala His Val
 1           5                   10                  15

GTC GCG AAC CCT CAA GCT GAG GGG CAG CTC CAG TGG CTG AAC CGC CGG       213
Val Ala Asn Pro Gln Ala Glu Gly Gln Leu Gln Trp Leu Asn Arg Arg
             20                  25                  30

GCC AAT GCC CTC CTG GCC AAT GGC GTG GAG CTG AGA GAT AAC CAG CTG       261
Ala Asn Ala Leu Leu Ala Asn Gly Val Glu Leu Arg Asp Asn Gln Leu
         35                  40                  45

GTG GTG CCA TCA GAG GGC CTG TAC CTC ATC TAC TCC CAG GTC CTC TTC       309
Val Val Pro Ser Glu Gly Leu Tyr Leu Ile Tyr Ser Gln Val Leu Phe
     50                  55                  60

AAG GGC CAA GGC TGC CCC TCC ACC CAT GTG CTC CTC ACC CAC ACC ATC       357
Lys Gly Gln Gly Cys Pro Ser Thr His Val Leu Leu Thr His Thr Ile
 65                  70                  75                  80

AGC CGC ATC GCC GTC TCC TAC CAG ACC AAG GTC AAC CTC CTC TCT GCC       405
Ser Arg Ile Ala Val Ser Tyr Gln Thr Lys Val Asn Leu Leu Ser Ala
                 85                  90                  95

ATC AAG AGC CCC TGC CAG AGG GAG ACC CCA GAG GGG GCT GAG GCC AAG       453
Ile Lys Ser Pro Cys Gln Arg Glu Thr Pro Glu Gly Ala Glu Ala Lys
            100                 105                 110

CCC TGG TAT GAG CCC ATC TAT CTG GGA GGG GTC TTC CAG CTG GAG AAG       501
Pro Trp Tyr Glu Pro Ile Tyr Leu Gly Gly Val Phe Gln Leu Glu Lys
        115                 120                 125

GGT GAC CGA CTC AGC GCT GAG ATC AAT CGG CCC GAC TAT CTC GAC TTT       549
Gly Asp Arg Leu Ser Ala Glu Ile Asn Arg Pro Asp Tyr Leu Asp Phe
130                 135                 140

GCC GAG TCT GGG CAG GTC TAC TTT GGG ATC ATT GCC CTG TGAGGAGGAC       598
Ala Glu Ser Gly Gln Val Tyr Phe Gly Ile Ile Ala Leu
145                 150                 155

GAACATCCAA CCTTCCCAAA CGCCTCCCCT GCCCCAATCC CTTTATTACC CCTCCTTCA      658

GACACCCTCA ACCTCTTCTG GCTCAAAAAG AGAATTGGGG GCTTAGGGTC GGAACCCAAG     718

CTTGGACTCC TGTTGATAGA TCCAGTAATG ACCTCAGAAC TCCATCTGGA TTTGTTCAGA    778

ACGCTCGGTT GCCGCCGGGC GTTTTTTATT GGTGAGAATC CAAGCTAGCT TGGCGAGATT    838

TTCAGGAGCT AAGGAAGCTA AAATGGAGAA AAAAATCACT GGATATACCA CCGTTGATAT    898

ATCCCAATGG CATCGTAAAG AACATTTTGA GGCATTTCAG TCAGTTGCTC AATGTACCTA    958
```

```
TAACCAGACC GTTCAGCTGG ATATTACGGC CTTTTTAAAG ACCGTAAAGA AAAATAAGCA   1018
CAAGTTTTAT CCGGCCTTTA TTCACATTCT TGCCCGCCTG ATGAATGCTC ATCCGGAATT   1078
TCGTATGGCA ATGAAAGACG GTGAGCTGGT GATATGGGAT AGTGTTCACC CTTGTTACAC   1138
CGTTTTCCAT GAGCAAACTG AAACGTTTTC ATCGCTCTGG AGTGAATACC ACGACGATTT   1198
CCGGCAGTTT CTACACATAT ATTCGCAAGA TGTGGCGTGT TACGGTGAAA ACCTGGCCTA   1258
TTTCCCTAAA GGGTTATTG AGAATATGTT TTCGTCTCA GCCAATCCCT GGGTGAGTTT     1318
CACCAGTTTT GATTTAAACG TGGCCAATAT GGACAACTTC TTCGCCCCCG TTTTCACCAT   1378
GGGCAAATAT TATACGCAAG GCGACAAGGT GCTGATGCCG CTGGCGATTC AGGTTCATCA   1438
TGCCGTCTGT GATGGCTTCC ATGTCGGCAG AATGCTTAAT GAATTACAAC AGTACTGCGA   1498
TGAGTGGCAG GGCGGGGCGT AATTTTTTA AGGCAGTTAT TGGTGCCCTT AAACGCCTGG    1558
GGTAATGACT CTCTAGCTTG AGGCATCAAA TAAAACGAAA GGCTCAGTCG AAAGACTGGG   1618
CCTTTCGTTT TATCTGTTGT TTGTCGGTGA ACGCTCTCCT GAGTAGGACA AATCCGCCGC   1678
TCTAGAGCTG CCTCGCGCGT TTCGGTGATG ACGGTGAAAA CCTCTGACAC ATGCAGCTCC   1738
CGGAGACGGT CACAGCTTGT CTGTAAGCGG ATGCCGGGAG CAGACAAGCC CGTCAGGGCG   1798
CGTCAGCGGG TGTTGGCGGG TGTCGGGGCG CAGCCATGAC CCAGTCACGT AGCGATAGCG   1858
GAGTGTATAC TGGCTTAACT ATGCGGCATC AGAGCAGATT GTACTGAGAG TGCACCATAT   1918
GCGGTGTGAA ATACCGCACA GATGCGTAAG GAGAAAATAC CGCATCAGGC GCTCTTCCGC   1978
TTCCTCGCTC ACTGACTCGC TGCGCTCGGT CTGTCGGCTG CGGCGAGCGG TATCAGCTCA   2038
CTCAAAGGCG GTAATACGGT TATCCACAGA ATCAGGGGAT AACGCAGGAA AGAACATGTG   2098
AGCAAAAGGC CAGCAAAAGG CCAGGAACCG TAAAAAGGCC GCGTTGCTGG CGTTTTTCCA   2158
TAGGCTCCGC CCCCCTGACG AGCATCACAA AAATCGACGC TCAAGTCAGA GGTGGCGAAA   2218
CCCGACAGGA CTATAAAGAT ACCAGGCGTT TCCCCCTGGA AGCTCCCTCG TGCGCTCTCC   2278
TGTTCCGACC CTGCCGCTTA CCGGATACCT GTCCGCCTTT CTCCCTTCGG GAAGCGTGGC   2338
GCTTTCTCAA TGCTCACGCT GTAGGTATCT CAGTTCGGTG TAGGTCGTTC GCTCCAAGCT   2398
GGGCTGTGTG CACGAACCCC CCGTTCAGCC CGACCGCTGC GCCTTATCCG GTAACTATCG   2458
TCTTGAGTCC AACCCGGTAA GACACGACTT ATCGCCACTG GCAGCAGCCA CTGGTAACAG   2518
GATTAGCAGA GCGAGGTATG TAGGCGGTGC TACAGAGTTC TTGAAGTGGT GGCCTAACTA   2578
CGGCTACACT AGAAGGACAG TATTTGGTAT CTGCGCTCTG CTGAAGCCAG TTACCTTCGG   2638
AAAAAGAGTT GGTAGCTCTT GATCCGGCAA ACAAACCACC GCTGGTAGCG GTGGTTTTTT   2698
TGTTTGCAAG CAGCAGATTA CGCGCAGAAA AAAAGGATCT CAAGAAGATC CTTTGATCTT   2758
TTCTACGGGG TCTGACGCTC AGTGGAACGA AAACTCACGT TAAGGGATTT TGGTCATGAG   2818
ATTATCAAAA AGGATCTTCA CCTAGATCCT TTTAAATTAA AAATGAAGTT TTAAATCAAT   2878
CTAAAGTATA TATGAGTAAA CTTGGTCTGA CAGTTACCAA TGCTTAATCA GTGAGGCACC   2938
TATCTCAGCG ATCTGTCTAT TTCGTTCATC CATAGCTGCC TGACTCCCCG TCGTGTAGAT   2998
AACTACGATA CGGGAGGGCT TACCATCTGG CCCCAGTGCT GCAATGATAC CGCGAGACCC   3058
ACGCTCACCG GCTCCAGATT TATCAGCAAT AAACCAGCCA GCCGGAAGGG CCGAGCGCAG   3118
AAGTGGTCCT GCAACTTTAT CCGCCTCCAT CCAGTCTATT AATTGTTGCC GGGAAGCTAG   3178
AGTAAGTAGT TCGCCAGTTA ATAGTTTGCG CAACGTTGTT GCCATTGCTA CAGGCATCGT   3238
GGTGTCACGC TCGTCGTTTG GTATGGCTTC ATTCAGCTCC GGTTCCCAAC GATCAAGGCG   3298
AGTTACATGA TCCCCCATGT TGTGCAAAAA AGCGGTTAGC TCCTTCGGTC CTCCGATCGT   3358
```

-continued

| | | | | | |
|---|---|---|---|---|---|
| TGTCAGAAGT | AAGTTGGCCG | CAGTGTTATC | ACTCATGGTT | ATGGCAGCAC | TGCATAATTC | 3418 |
| TCTTACTGTC | ATGCCATCCG | TAAGATGCTT | TTCTGTGACT | GGTGAGTACT | CAACCAAGTC | 3478 |
| ATTCTGAGAA | TAGTGTATGC | GGCGACCGAG | TTGCTCTTGC | CCGGCGTCAA | TACGGGATAA | 3538 |
| TACCGCGCCA | CATAGCAGAA | CTTTAAAAGT | GCTCATCATT | GGAAAACGTT | CTTCGGGGCG | 3598 |
| AAAACTCTCA | AGGATCTTAC | CGCTGTTGAG | ATCCAGTTCG | ATGTAACCCA | CTCGTGCACC | 3658 |
| CAACTGATCT | TCAGCATCTT | TTACTTTCAC | CAGCGTTTCT | GGGTGAGCAA | AAACAGGAAG | 3718 |
| GCAAAATGCC | GCAAAAAAGG | GAATAAGGGC | GACACGGAAA | TGTTGAATAC | TCATACTCTT | 3778 |
| CCTTTTTCAA | TATTATTGAA | GCATTTATCA | GGGTTATTGT | CTCATGAGCG | GATACATATT | 3838 |
| TGAATGTATT | TAGAAAAATA | AACAAATAGG | GGTTCCGCGC | ACATTTCCCC | GAAAAGTGCC | 3898 |
| ACCTGACGTC | TAAGAAACCA | TTATTATCAT | GACATTAACC | TATAAAAATA | GGCGTATCAC | 3958 |
| GAGGCCCTTT | CGTCTTCAC | | | | | 3977 |

( 2 ) INFORMATION FOR SEQ ID NO:2:

( i ) SEQUENCE CHARACTERISTICS:
        ( A ) LENGTH: 157 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

( 2 ) INFORMATION FOR SEQ ID NO:3:

( i ) SEQUENCE CHARACTERISTICS:
        ( A ) LENGTH: 3740 base pairs
        ( B ) TYPE: nucleic acid
        ( C ) STRANDEDNESS: single
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: plasmid pREP4

(xi) SEQUENCE DESCRIPTION: SEQ ID NO:3:

```
AAGCTTCACG CTGCCGCAAG CACTCAGGGC GCAAGGGCTG CTAAAGGAAG CGGAACACGT      60
AGAAAGCCAG TCCGCAGAAA CGGTGCTGAC CCCGGATGAA TGTCAGCTAC TGGGCTATCT     120
GGACAAGGGA AAACGCAAGC GCAAAGAGAA AGCAGGTAGC TTGCAGTGGG CTTACATGGC     180
GATAGCTAGA CTGGGCGGTT TTATGGACAG CAAGCGAACC GGAATTGCCA GCTGGGGCGC     240
CCTCTGGTAA GGTTGGGAAG CCCTGCAAAG TAAACTGGAT GGCTTTCTTG CCGCCAAGGA     300
TCTGATGGCG CAGGGGATCA AGATCTGATC AAGAGACAGG ATGACGGTCG TTTCGCATGC     360
TTGAACAAGA TGGATTGCAC GCAGGTTCTC CGGCCGCTTG GGTGGAGAGG CTATTCGGCT     420
ATGACTGGGC ACAACAGACA ATCGGCTGCT CTGATGCCGC CGTGTTCCGG CTGTCAGCGC     480
AGGGGCGCCC GGTTCTTTTT GTCAAGACCG ACCTGTCCGG TGCCCTGAAT GAACTGCAGG     540
ACGAGGCAGC GCGGCTATCG TGGCTGGCCA CGACGGGCGT TCCTTGCGCA GCTGTGCTCG     600
ACGTTGTCAC TGAAGCGGGA AGGGACTGGC TGCTATTGGG CGAAGTGCCG GGGCAGGATC     660
TCCTGTCATC TCACCTTGCT CCTGCCGAGA AAGTATCCAT CATGGCTGAT GCAATGCGGC     720
GGCTGCATAC GCTTGATCCG GCTACCTGCC CATTCGACCA CCAAGCGAAA CATCGCATCG     780
AGCGAGCACG TACTCGGATG GAAGCCGGTC TTGTCGATCA GGATGATCTG GACGAAGAGC     840
ATCAGGGGCT CGCGCCAGCC GAACTGTTCG CCAGGCTCAA GGCGCGCATG CCCGACGGCG     900
AGGATCTCGT CGTGACCCAT GGCGATGCCT GCTTGCCGAA TATCATGGTG GAAAATGGCC     960
GCTTTTCTGG ATTCATCGAC TGTGGCCGGC TGGGTGTGGC GGACCGCTAT CAGGACATAG    1020
CGTTGGCTAC CCGTGATATT GCTGAAGAGC TTGGCGGCGA ATGGGCTGAC CGCTTCCTCG    1080
TGCTTTACGG TATCGCCGCT CCCGATTCGC AGCGCATCGC CTTCTATCGC CTTCTTGACG    1140
AGTTCTTCTG AGCGGGACTC TGGGGTTCGA AATGACCGAC CAAGCGACGC CCAACCTGCC    1200
ATCACGAGAT TTCGATTCCA CCGCCGCCTT CTATGAAAGG TTGGGCTTCG GAATCGTTTT    1260
CCGGGACGCC GGCTGGATGA TCCTCCAGCG CGGGGATCTC ATGCTGGAGT TCTTCGCCCA    1320
CCCCGGGCTC GATCCCCTCG CGAGTTGGTT CAGCTGCTGC CTGAGGCTGG ACGACCTCGC    1380
GGAGTTCTAC CGGCAGTGCA AATCCGTCGG CATCCAGGAA ACCAGCAGCG GCTATCCGCG    1440
CATCCATGCC CCCGAACTGC AGGAGTGGGG AGGCACGATG GCCGCTTTGG TCGACAATTC    1500
GCGCTAACTT ACATTAATTG CGTTGCGCTC ACTGCCCGCT TTCCAGTCGG GAAACCTGTC    1560
GTGCCAGCTG CATTAATGAA TCGGCCAACG CGCGGGGAGA GGCGGTTTGC GTATTGGGCG    1620
CCAGGGTGGT TTTTCTTTTC ACCAGTGAGA CGGGCAACAG CTGATTGCCC TTCACCGCCT    1680
GGCCCTGAGA GAGTTGCAGC AAGCGGTCCA CGCTGGTTTG CCCCAGCAGG CGAAAATCCT    1740
GTTTGATGGT GGTTAACGGC GGGATATAAC ATGAGCTGTC TTCGGTATCG TCGTATCCCA    1800
CTACCGAGAT ATCCGCACCA ACGCGCAGCC CGGACTCGGT AATGGCGCGC ATTGCGCCCA    1860
GCGCCATCTG ATCGTTGGCA ACCAGCATCG CAGTGGGAAC GATGCCCTCA TTCAGCATTT    1920
GCATGGTTTG TTGAAAACCG GACATGGCAC TCCAGTCGCC TTCCCGTTCC GCTATCGGCT    1980
GAATTTGATT GCGAGTGAGA TATTTATGCC AGCCAGCCAG ACGCAGACGC GCCGAGACAG    2040
AACTTAATGG GCCCGCTAAC AGCGCGATTT GCTGGTGACC CAATGCGACC AGATGCTCCA    2100
CGCCCAGTCG CGTACCGTCT TCATGGGAGA AAATAATACT GTTGATGGGT GTCTGGTCAG    2160
AGACATCAAG AAATAACGCC GGAACATTAG TGCAGGCAGC TTCCACAGCA ATGGCATCCT    2220
GGTCATCCAG CGGATAGTTA ATGATCAGCC CACTGACGCG TTGCGCGAGA AGATTGTGCA    2280
```

-continued

| | | | | | | |
|---|---|---|---|---|---|---|
| CCGCCGCTTT | ACAGGCTTCG | ACGCCGCTTC | GTTCTACCAT | CGACACCACC | ACGCTGGCAC | 2340 |
| CCAGTTGATC | GGCGCGAGAT | TTAATCGCCG | CGACAATTTG | CGACGGCGCG | TGCAGGGCCA | 2400 |
| GACTGGAGGT | GGCAACGCCA | ATCAGCAACG | ACTGTTTGCC | CGCCAGTTGT | TGTGCCACGC | 2460 |
| GGTTGGGAAT | GTAATTCAGC | TCCGCCATCG | CCGCTTCCAC | TTTTTCCCGC | GTTTTCGCAG | 2520 |
| AAACGTGGCT | GGCCTGGTTC | ACCACGCGGG | AAACGGTCTG | ATAAGAGACA | CCGGCATACT | 2580 |
| CTGCGACATC | GTATAACGTT | ACTGGTTTCA | CATTCACCAC | CCTGAATTGA | CTCTCTTCCG | 2640 |
| GGCGCTATCA | TGCCATACCG | CGAAAGGTTT | TGCGCCATTC | GATGGTGTCA | ACGTAAATGC | 2700 |
| ATGCCGCTTC | GCCTTCGCGC | GCGAATTGTC | GACCCTGTCC | CTCCTGTTCA | GCTACTGACG | 2760 |
| GGGTGGTGCG | TAACGGCAAA | AGCACCGCCG | GACATCAGCG | CTAGCGGAGT | GTATACTGGC | 2820 |
| TTACTATGTT | GGCACTGATG | AGGGTGTCAG | TGAAGTGCTT | CATGTGGCAG | GAGAAAAAAG | 2880 |
| GCTGCACCGG | TGCGTCAGCA | GAATATGTGA | TACAGGATAT | ATTCCGCTTC | CTCGCTCACT | 2940 |
| GACTCGCTAC | GCTCGGTCGT | TCGACTGCGG | CGAGCGGAAA | TGGCTTACGA | ACGGGGCGGA | 3000 |
| GATTTCCTGG | AAGATGCCAG | GAAGATACTT | AACAGGGAAG | TGAGAGGGCC | GCGGCAAAGC | 3060 |
| CGTTTTTCCA | TAGGCTCCGC | CCCCCTGACA | AGCATCACGA | AATCTGACGC | TCAAATCAGT | 3120 |
| GGTGGCGAAA | CCCGACAGGA | CTATAAAGAT | ACCAGGCGTT | TCCCCTGGCG | GCTCCCTCGT | 3180 |
| GCGCTCTCCT | GTTCCTGCCT | TTCGGTTTAC | CGGTGTCATT | CCGCTGTTAT | GGCCGCGTTT | 3240 |
| GTCTCATTCC | ACGCCTGACA | CTCAGTTCCG | GGTAGGCAGT | TCGCTCCAAG | CTGGACTGTA | 3300 |
| TGCACGAACC | CCCCGTTCAG | TCCGACCGCT | GCGCCTTATC | CGGTAACTAT | CGTCTTGAGT | 3360 |
| CCAACCCGGA | AAGACATGCA | AAAGCACCAC | TGGCAGCAGC | CACTGGTAAT | TGATTTAGAG | 3420 |
| GAGTTAGTCT | TGAAGTCATG | CGCCGGTTAA | GGCTAAACTG | AAAGGACAAG | TTTTGGTGAC | 3480 |
| TGCGCTCCTC | CAAGCCAGTT | ACCTCGGTTC | AAAGAGTTGG | TAGCTCAGAG | AACCTTCGAA | 3540 |
| AAACCGCCCT | GCAAGGCGGT | TTTTTCGTTT | TCAGAGCAAG | AGATTACGCG | CAGACCAAAA | 3600 |
| CGATCTCAAG | AAGATCATCT | TATTAATCAG | ATAAAATATT | TCTAGATTTC | AGTGCAATTT | 3660 |
| ATCTCTTCAA | ATGTAGCACC | TGAAGTCAGC | CCCATACGAT | ATAAGTTGTT | AATTCTCATG | 3720 |
| TTTGACAGCT | TATCATCGAT | | | | | 3740 |

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: primer 17/F ( x i ) SEQUENCE DESCRIPTION: SEQ ID NO:4:

GGCGTATCAC GAGGCCCTTT CG                         22

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: primer 46/M12

(xi) SEQUENCE DESCRIPTION: SEQ ID NO:5:

GCGAAAGTTG AGATAGTCGG GCCGATTG                    28

(2) INFORMATION FOR SEQ ID NO:6:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: primer 29/MR2

(xi) SEQUENCE DESCRIPTION: SEQ ID NO:6:

GAGTCTGGGC AGGTCTACTT TG                         22

(2) INFORMATION FOR SEQ ID NO:7:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: primer 17/O (xi) SEQUENCE DESCRIPTION: SEQ ID NO:7:

CATTACTGGA TCTATCAACA GG                         22